United States Patent
Cochran et al.

(10) Patent No.: US 10,844,106 B2
(45) Date of Patent: Nov. 24, 2020

(54) FUSION PROTEINS COMPRISING AN ENGINEERED KNOTTIN PEPTIDE AND USES THEREOF

(75) Inventors: Jennifer R. Cochran, Stanford, CA (US); Douglas S. Jones, Cambridge, MA (US); Mihalis S. Kariolis, Stanford, CA (US); Ping-Chuan Tsai, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1320 days.

(21) Appl. No.: 13/883,216

(22) PCT Filed: Nov. 7, 2011

(86) PCT No.: PCT/US2011/059599
§ 371 (c)(1),
(2), (4) Date: Nov. 20, 2013

(87) PCT Pub. No.: WO2012/064658
PCT Pub. Date: May 18, 2012

(65) Prior Publication Data
US 2014/0073518 A1    Mar. 13, 2014

Related U.S. Application Data

(60) Provisional application No. 61/411,350, filed on Nov. 8, 2010.

(51) Int. Cl.
| | | |
|---|---|---|
| *C07K 14/705* | (2006.01) | |
| *C07K 14/71* | (2006.01) | |
| *C07K 14/47* | (2006.01) | |
| *C07K 14/81* | (2006.01) | |
| *C07K 14/435* | (2006.01) | |
| *C07K 14/475* | (2006.01) | |

(52) U.S. Cl.
CPC ...... *C07K 14/705* (2013.01); *C07K 14/43518* (2013.01); *C07K 14/47* (2013.01); *C07K 14/4702* (2013.01); *C07K 14/475* (2013.01); *C07K 14/71* (2013.01); *C07K 14/81* (2013.01); *C07K 14/8121* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,468,634 A | 11/1995 | Liu | |
| 6,423,538 B1 | 7/2002 | Wittrup et al. | |
| 7,674,881 B2 | 3/2010 | Kent et al. | |
| 8,329,826 B2 | 12/2012 | Hartmann et al. | |
| 8,536,301 B2 | 9/2013 | Cochran et al. | |
| 8,618,254 B2 | 12/2013 | Giaccia et al. | |
| 10,350,266 B2* | 7/2019 | Cochran | A61K 39/39541 |
| 2004/0106118 A1 | 6/2004 | Kolmar et al. | |
| 2004/0132634 A1 | 7/2004 | Sicheri et al. | |
| 2004/0236073 A1 | 11/2004 | Gherardi et al. | |
| 2006/0040325 A1* | 2/2006 | Wu | C07K 16/00 435/7.1 |
| 2009/0155275 A1 | 6/2009 | Wu et al. | |
| 2009/0257952 A1 | 10/2009 | Cochran et al. | |
| 2010/0267610 A1 | 10/2010 | Blind et al. | |
| 2011/0091412 A1* | 4/2011 | Wittrup | C07K 14/55 424/85.2 |
| 2011/0136740 A1 | 6/2011 | Cochran et al. | |
| 2012/0058907 A1 | 3/2012 | Logtenberg et al. | |

FOREIGN PATENT DOCUMENTS

| | | |
|---|---|---|
| WO | 00/44898 A2 | 8/2000 |
| WO | 0234906 A2 | 5/2002 |
| WO | 2005/068622 A2 | 7/2005 |
| WO | 2008/045252 A2 | 4/2008 |
| WO | 2009/005813 A1 | 8/2009 |
| WO | 2010/048588 A2 | 4/2010 |

OTHER PUBLICATIONS

Meropol et al (Clinical Cancer Research 2:669-77) (Year: 1996).*
Wikigenes—Gene review AGA2-Aga2p [retrieved from internet Dec. 4, 2015]. <URL:https://www.wikigenes.org/e/gene/e/852851.html, 2 pp.
Holland et al., "Multiple roles for the receptor tyrosine kinase axl in tumor formation", Cancer Res. Oct. 15, 2005, vol. 65, No. 20, pp. 9294-9303.
International Search Report and Written Opinion, PCT/US11/59599, dated Mar. 19, 2012.
Gelly, et al., "The KNOTTIN website and database: a new information system dedicated to the knottin scaffold" Nucleic Acids Research, 2004, vol. 32, Database issue—D156-D159.
Christmann, et al., "The cystine know of a squash-type protease inhibitor as a structural scaffold for *Escherichia coli* cell surface display of conformationally constrained peptides" Protein Engineering, vol. 12, No. 9, pp. 797-806, 1999.

(Continued)

*Primary Examiner* — Christopher M Gross
(74) *Attorney, Agent, or Firm* — Brian E. Davy; Bozicevic, Field & Francis LLP

(57) ABSTRACT

The present disclosure presents a general approach to engineering existing protein-protein interactions through domain addition and evolution. The disclosure teaches the creation of novel fusion proteins that include knottin peptides where a portion of the knottin peptide is replaced with a sequence that has been created for binding to a particular target. Such fusion proteins can also be bispecific or multi specific in that they can bind to and/or inhibit two or more receptors or receptor ligands. Knottins may be fused with an existing ligand (or receptor) as a general platform for increasing the affinity of a ligand-receptor interaction or for creating a multi specific protein. In addition, the fusion proteins may comprise a knottin peptide fused to another protein where the other protein facilitates proper expression and folding of the knottin.

24 Claims, 14 Drawing Sheets

Specification includes a Sequence Listing.

(56) References Cited

OTHER PUBLICATIONS

Kimura, et al., "Functional mutation of multiple solvent-exposed loops in the Ecballium elaterium trypsin inhibitor-II cyctine knot miniprotein", PLoS ONE, Feb. 2011, vol. 6, Issue 2, pp. 1-11.

Jones, et al., "Engineering hepatocyte growth factor fragments with high stability and activity as Met receptor agonists and antagonists", PNAS, Aug. 9, 2011, vol. 108, No. 32, 13035-13040.

Daly, et al., "Disulfide folding pathways of cystine knot proteins", The Journal of Biological Chemistry, vol. 278, No. 8, Feb. 21, 2003, pp. 6314-6322.

Hwang, et al., "Isolation and characterization of psacotheasin, a novel knottin-type antimicrobial peptide, from Psacothea hilaris", Journal of Microbiology and Biotechnology, (2010), 20(4), 708-711.

Leitha, et al., "Crystal structures of NK1-heparin complexes reveal the basis for NK1 activity and enable engineering of potent agonists of the MET receptor", The EMBO Journal, vol. 20, No. 20, pp. 5543-5555, 2001.

Skerra, Arne, "Engineered protein scaffolds for molecular recognition", Journal of Molecular Recognition, 2000;13:167-187.

Yeh, et al., "Rhodotomin, a snake venom disintegrin, inhibits angiogenesis elicited by basic fibroblast growth factor and suppresses tumor growth by a selective alphvbeta3 blockade of endothelial cells," Molecular Pharmacology, vol. 59, No. 5, 2001, pp. 1333-1342.

Supplemental European Search Report, Application No. 11839687.8, dated Mar. 14, 2014.

Wentzel, et al., "Display of Passenger Proteins on the Surface of *Escherichia coli* K-12 by the Enterohemorrhagic *E. coli* Intimin EaeA", Journal of Bacteriology, American Society for Microbiology, vol. 183, No. 24, Dec. 1, 2001, pp. 7273-7284.

Silverman, et al., "Cystine-knot peptides engineered with specificities for $\alpha$IIb$\beta$3 or $\alpha$IIb$\beta$3 and $\alpha$v$\beta$3 integrins are potent inhibitors of platelet aggregation", Journal of Molecular Recognition, vol. 24, No. 1, May 5, 2010, pp. 127-135.

Kimura, et al., "Engineered cystine knot peptides that bind $\alpha$v$\beta$3, $\alpha$v$\beta$5, and $\alpha$5$\beta$1 integrins with low-nanomolar affinity", Proteins: Structure, Function, and Bioinformatics, vol. 77, No. 2, Nov. 1, 2009, pp. 359-369.

Reiss, et al., "Inhibition of platelet aggregation by grafting RGD and KGD sequences on the structural scaffold of small disulfide-rich proteins", Platelets, Taylor and Francis Group, May 2006, 17(3): 153-157.

English Translation, JP Official Action, JP Patent Appl. No. 2013-537908, dated Oct. 20, 2015, 6 pp.

Jiang et al. (2012) "111In-Labeled Cystine-Knot Peptides Based on the Agouti-Related Protein for Targeting Tumor Angiogenesis" J. of Biomed. and Biotech., Article ID 368075, 8 pgs.

Miao et al. (2011) "Protein scaffold-based molecular probes for cancer molecular imaging" Amino Acids, 41:1037-1047.

Moore et al. (2013) "Engineering Agatoxin, a Cystine-Knot Peptide from Spider Venom, as a Molecular Probe for In Vivo Tumor Imaging" PLOS ONE, 8(4):e60498.

Moore et al. (2013) "Engineered knottin peptide enables noninvasive optical imaging of intracranial medulloblastoma" PNAS, 110(36):14598-14603.

Anonymous, "IgG-Fc engineering for therapeutic use," (Apr. 1, 2006) Retrieved from the internet:URL:http://www.invivogen.com/docs/Insight200605.pdf.

Huang, T.-H., "A Trimeric Anti-HER2/neu ScFv and Tumor Necrosis Factor-$\alpha$ Fusion Protein Induces HER2/neu Signaling an Facilitates Repair of Injured Epithelia," Journal of Pharmacology and Experimental Thereapeutics (Nov. 11, 2005) 316(3):983-991.

\* cited by examiner

EETI-II (SEQ ID NO: 2)   GC*PRILMR* --- CKQDSDCLAGCVC*GPNGF* ---- CGSP
                           \Randomize/              \Randomize/
                            Loop 1                   Loop 3

E-Axl                   GC (X)$_n$ ----- CKQDSDCLAGCVC (X)$_m$ ----- CGS.RGTQAE...
library (SEQ ID NO: 81)
                        n = 7-10              Library              Axl Ig1
                        m = 6-8              Screening EA 7.01 (SEQ ID NO: 41)  GC  ALMTPSAVD   CKQDSDCLAGCVC  LPGMVR      CGS.RGTQAE....
EA 7.06 (SEQ ID NO: 46)  GC  LGGVALAH    CKQDSDCLAGCVC  HILPEL      CGS.RGTQAE....
EA 8.04 (SEQ ID NO: 50)  GC  SWSTLAR     CKQDSDCLAGCVC  MLEPGMRS    CGS.RGTQAE....

P-G/T-M/K Motif    EA 7.01 (residues 25-30 of SEQ ID NO: 41)     LPGMVR
in Loop 3          EA 7.03 (residues 23-30 of SEQ ID NO: 43)     TLLPGMLM
                   EA 7.05 (residues 23-30 of SEQ ID NO: 45)     ILDPGKRS
                   EA 8.04 (residues 23-30 of SEQ ID NO: 50)     MLEPGMRS
                   EA 8.05 (residues 23-30 of SEQ ID NO: 51)     YLCPTMGS GS. = end of EETI
portion

Figure 1D

```
                               SEQUENCE LISTING

<160> NUMBER OF SEQ ID NOS: 89

<210> SEQ ID NO 1
    <211> LENGTH: 28
    <212> TYPE: PRT
    <213> ORGANISM: Ecballium elaterium

<400> SEQUENCE: 1

Gly Cys Pro Arg Ile Leu Met Arg Cys Lys Gln Asp Ser Asp Cys Leu
    1               5                   10                  15

Ala Gly Cys Val Cys Gly Pro Asn Gly Phe Cys Gly
                20                  25

<210> SEQ ID NO 2
    <211> LENGTH: 30
    <212> TYPE: PRT
    <213> ORGANISM: Ecballium elaterium

<400> SEQUENCE: 2

Gly Cys Pro Arg Ile Leu Met Arg Cys Lys Gln Asp Ser Asp Cys Leu
    1               5                   10                  15

Ala Gly Cys Val Cys Gly Pro Asn Gly Phe Cys Gly Ser Pro
                20                  25                  30

<210> SEQ ID NO 3
    <211> LENGTH: 47
    <212> TYPE: PRT
    <213> ORGANISM: Artificial Sequence
    <220> FEATURE:
    <223> OTHER INFORMATION: Description of Artificial Sequence: Synthetic
          polypeptide

<400> SEQUENCE: 3

Gly Cys Val Arg Leu His Glu Ser Cys Leu Gly Gln Gln Val Pro Cys
    1               5                   10                  15

Cys Asp Pro Cys Ala Thr Cys Tyr Cys Arg Phe Phe Asn Ala Phe Cys
                20                  25                  30

Tyr Cys Arg Lys Leu Gly Thr Ala Met Asn Pro Cys Ser Arg Thr
                35                  40                  45

<210> SEQ ID NO 4
    <211> LENGTH: 35
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Cys Val Arg Leu His Glu Ser Cys Leu Gly Gln Gln Val Pro Cys
1               5                   10                  15

Cys Asp Pro Ala Ala Thr Cys Tyr Cys Arg Phe Phe Asn Ala Phe Cys
                20                  25                  30

Tyr Cys Arg
        35

<210> SEQ ID NO 5
<211> LENGTH: 48
<212> TYPE: PRT
<213> ORGANISM: Agelenopsis aperta

<400> SEQUENCE: 5

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
                20                  25                  30

Asn Cys Glu Cys Thr Pro Arg Leu Ile Met Glu Gly Leu Ser Phe Ala
            35                  40                  45

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
                20                  25                  30

Gly

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
                20                  25                  30

Gly

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 8

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Cys Asn Val Gly Arg Gly Asp Trp Ala Pro Ser Glu Cys Lys Gln
1               5                   10                  15
```

Asp Ser Asp Cys Pro Ala Gly Cys Val Cys Gly Pro Asn Gly Phe Cys
            20                  25                  30

Gly

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Cys Pro Leu Pro Arg Gly Asp Asn Pro Pro Thr Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 20
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Gly Pro Asn Gly Phe Cys
            20                  25                  30

Gly

```
<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

```
<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22
```

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

```
<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23
```

Gly Cys Leu Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

```
<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

```
<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Cys Tyr Gln Gly Arg Gly Asp Trp Ser Pro Ser Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 28
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 29
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Cys Val Gln Gly Arg Gly Asp Trp Ser Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 30
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Cys Asp Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 33
<211> LENGTH: 33
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 33

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 34
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 35
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 36
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
            35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 37

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Ala Arg
                20                  25                  30

Leu Gln Cys Tyr Cys Arg
            35

<210> SEQ ID NO 38
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asp Asn
                20                  25                  30

Leu Lys Cys Tyr Cys Arg
            35

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Arg Asp
                20                  25                  30

Met Lys Cys Tyr Cys Arg
            35

<210> SEQ ID NO 40
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 tctagg                                                          6

<210> SEQ ID NO 41
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Cys Ala Leu Met Thr Pro Ser Ala Val Asp Cys Lys Gln Asp Ser
1               5                   10                  15

```
Asp Cys Leu Ala Gly Cys Val Cys Leu Pro Gly Met Val Arg Cys Gly
            20                  25                  30

Ser Arg Gly Thr Gln Ala Glu Glu Ser Pro Phe Val Ser Asn Pro
        35                  40                  45

Gly Asn Ile Thr Gly Ala Arg Gly Leu Thr Gly Thr Leu Arg Cys Gln
    50                  55                  60

Leu Gln Val Gln Gly Glu Pro Pro Glu Val His Trp Leu Arg Asp Gly
65                  70                  75

Gln Ile Leu Glu Leu Ala Asp Ser Thr Gln Thr Gln Val Pro Leu Gly
80                  85                  90                  95

Glu Asp Glu Gln Gly Asp Trp Ile Val Ala Ser Gln Leu Arg Ile Thr
                100                 105                 110

Ser Leu Gln Leu Ser Asp Thr Gly Gln Tyr Gln Cys Leu Val Phe Leu
            115                 120                 125

Gly His Gln Thr Phe Val Ser Gln Pro Gly Tyr Val Arg Leu Glu Gly
        130                 135                 140

Leu Pro
    145

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Cys Leu Gly Asn Val Arg Ala Cys Val Ser Val Cys Lys Gln Asp
1               5                   10                  15

Ser Asp Cys Leu Ala Gly Cys Val Cys Glu Leu Ala Arg Ser Asn Lys
            20                  25                  30

Cys Cys Gly Ser
        35

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Cys Thr Ala Val Arg Pro Cys Thr Cys Lys Gln Asp Ser Asp Cys
1               5                   10                  15

Leu Ala Gly Cys Val Cys Thr Leu Leu Pro Gly Met Leu Met Cys Gly
            20                  25                  30

Ser

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Cys Trp Pro Arg Val Ser Cys Val Leu Trp His Cys Lys Gln Asp
1               5                   10                  15
```

```
Ser Asp Cys Leu Ala Gly Cys Val Cys Ile Leu Thr Arg His Lys Thr
            20                  25                  30

Val Cys Gly Ser
            35

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Arg Arg Trp Trp Thr Leu Ala Arg Cys Lys Gln Asp Ser Asp Cys
1               5                   10                  15

Leu Ala Gly Cys Val Cys Ile Leu Asp Pro Gly Lys Arg Ser Cys Gly
            20                  25                  30

Ser

<210> SEQ ID NO 46
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Cys Leu Gly Gly Val Ala Leu Ala His Cys Lys Gln Asp Ser Asp
1               5                   10                  15

Cys Leu Ala Gly Cys Val Cys His Ile Leu Pro Glu Leu Cys Gly Ser
            20                  25                  30

Arg Gly Thr Gln Ala Glu Glu Ser Pro Phe Val Ser Asn Pro
            35                  40                  45

Gly Asn Ile Thr Gly Ala Arg Gly Leu Thr Gly Thr Leu Arg Cys Gln
        50                  55                  60

Leu Gln Val Gln Gly Glu Pro Pro Glu Val His Trp Leu Arg Asp Gly
    65                  70                  75

Gln Ile Leu Glu Leu Ala Asp Ser Thr Gln Thr Gln Val Pro Leu Gly
        80                  85                  90

Glu Asp Glu Gln Gly Asp Trp Ile Val Ala Ser Gln Leu Arg Ile Thr
    95                  100                 105                 110

Ser Leu Gln Leu Ser Asp Thr Gly Gln Tyr Gln Cys Leu Val Phe Leu
                115                 120                 125

Gly His Gln Thr Phe Val Ser Gln Pro Gly Tyr Val Arg Leu Glu Gly
            130                 135                 140

Leu Pro

<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Cys His Glu Asn Gly Leu Pro Leu Ile Cys Lys Gln Asp Ser Asp
1               5                   10                  15
```

```
Cys Leu Ala Gly Cys Val Cys Ser Ser His Asn Trp Cys Gln Cys Gly
            20                  25                  30

Ser

<210> SEQ ID NO 48
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Cys Ala Leu Met Thr Pro Ser Ala Val Asp Cys Lys Gln Asp Ser
1               5                   10                  15

Asp Cys Leu Ala Gly Cys Val Cys Leu Pro Gly Met Val Arg Cys Gly
            20                  25                  30

Ser

<210> SEQ ID NO 49
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Cys Val Cys Leu Cys Cys Gly Pro Ser Gly Ser Cys Lys Gln Asp
1               5                   10                  15

Ser Asp Cys Leu Ala Gly Cys Val Cys Ala Ala Asn His Lys Asp Asn
            20                  25                  30

Cys Gly Ser
        35

<210> SEQ ID NO 50
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Cys Ser Trp Ser Thr Leu Ala Arg Cys Lys Gln Asp Ser Asp Cys
1               5                   10                  15

Leu Ala Gly Cys Val Cys Met Leu Glu Pro Gly Met Arg Ser Cys Gly
            20                  25                  30

Ser Arg Gly Thr Gln Ala Glu Glu Ser Pro Phe Val Ser Asn Pro
            35                  40                  45

Gly Asn Ile Thr Gly Ala Arg Gly Leu Thr Gly Thr Leu Arg Cys Gln
        50                  55                  60

Leu Gln Val Gln Gly Glu Pro Pro Glu Val His Trp Leu Arg Asp Gly
65                  70                  75

Gln Ile Leu Glu Leu Ala Asp Ser Thr Gln Thr Gln Val Pro Leu Gly
80                  85                  90                  95

Glu Asp Glu Gln Gly Asp Trp Ile Val Ala Ser Gln Leu Arg Ile Thr
                100                 105                 110

Ser Leu Gln Leu Ser Asp Thr Gly Gln Tyr Gln Cys Leu Val Phe Leu
                115                 120                 125
```

Gly His Gln Thr Phe Val Ser Gln Pro Gly Tyr Val Arg Leu Glu Gly
        130                 135                 140

Leu Pro
    145

<210> SEQ ID NO 51
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Cys Trp Leu Glu Cys Trp Tyr Arg Cys Lys Gln Asp Ser Asp Cys
1               5                   10                  15

Leu Ala Gly Cys Val Cys Tyr Leu Cys Pro Thr Met Gly Ser Cys Gly
            20                  25                  30

Ser

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Cys Leu Gly Asn Val Arg Ala Cys Val Ser Val Cys Lys Gln Asp
1               5                   10                  15

Ser Asp Cys Leu Ala Gly Cys Val Cys Glu Leu Ala Arg Ser Asn Lys
            20                  25                  30

Cys Cys Gly Ser
        35

<210> SEQ ID NO 53
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Cys Val Arg Val Ala Ser His Leu Trp Phe Cys Lys Gln Asp Ser
1               5                   10                  15

Asp Cys Leu Ala Gly Cys Val Cys Cys Gly Arg Pro Asn Val Cys Gly
            20                  25                  30

Ser

<210> SEQ ID NO 54
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Cys Val Cys Leu Cys Cys Gly Pro Ser Gly Ser Cys Lys Gln Asp
1               5                   10                  15

Ser Asp Cys Leu Ala Gly Cys Val Ala Ala Asn His Lys Asp Asn
            20                  25                  30

Cys Gly Ser
        35

<210> SEQ ID NO 55
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Cys Cys Ser Leu Arg Trp Cys Val Ser Arg Val Cys Lys Gln Asp
1               5                   10                  15

Ser Asp Cys Leu Ala Gly Cys Val Cys Ile Asn Pro Asn Lys Pro Leu
            20                  25                  30

Cys Gly Ser
        35

<210> SEQ ID NO 56
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Cys Ala Leu Met Thr Pro Ser Ala Val Asp Cys Lys Gln Asp Ser
1               5                   10                  15

Asp Cys Leu Ala Gly Cys Val Cys Leu Pro Gly Met Val Arg Cys Gly
            20                  25                  30

Ser

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Cys Val Arg Val Ala Ser His Leu Trp Phe Cys Lys Gln Asp Ser
1               5                   10                  15

Asp Cys Leu Ala Gly Cys Val Cys Cys Gly Arg Pro Asn Val Cys Gly
            20                  25                  30

Ser

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Cys Cys Ser Leu Arg Trp Cys Val Ser Arg Val Cys Lys Gln Asp
1               5                   10                  15

Ser Asp Cys Leu Ala Gly Cys Val Cys Ile Asn Pro Asn Lys Pro Leu

```
                      20                  25                  30

Cys Gly Ser
        35

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Pro Gln Gly Arg Gly Asp Trp Ala Pro Thr Ser Cys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Pro Arg Pro Arg Gly Asp Asn Pro Pro Leu Thr Cys
1               5                   10

<210> SEQ ID NO 61
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro

<210> SEQ ID NO 62
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Pro Arg Gly Thr Gln Ala Glu Glu Ser Pro Phe Val Ser Asn Pro
```

```
                1               5                   10                  15
Gly Asn Ile Thr Gly Ala Arg Gly Leu Thr Gly Thr Leu Arg Cys Gln
                20                  25                  30

Leu Gln Val Gln Gly Glu Pro Pro Glu Val His Trp Leu Arg Asp Gly
            35                  40                  45

Gln Ile Leu Glu Leu Ala Asp Ser Thr Gln Thr Val Pro Leu Gly
        50                  55                  60

Glu Asp Glu Gln Gly Asp Trp Ile Val Ala Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Arg Leu Glu Gly
            100                 105                 110

Leu Pro

<210> SEQ ID NO 63
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Pro Arg Gly Thr Gln Ala Gly Glu Ser Pro Phe Val Gly Asn Pro
1               5                   10                  15

Gly Asn Ile Thr Gly Ala Arg Gly Leu Thr Gly Thr Leu Arg Cys Gln
                20                  25                  30

Leu Gln Val Gln Gly Glu Pro Pro Glu Val His Trp Leu Arg Asp Gly
            35                  40                  45

Gln Ile Leu Glu Leu Ala Asp Ser Thr Gln Thr Gln Met Pro Leu Gly
        50                  55                  60

Glu Asp Glu Gln Asp Asp Trp Ile Val Ala Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Glu Leu Glu Gly
            100                 105                 110

Leu Pro

<210> SEQ ID NO 64
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gly Cys Pro Gln Gly Arg Gly Asp Trp Ala Pro Thr Ser Cys Lys Gln
1               5                   10                  15

Asp Ser Asp Cys Leu Ala Gly Cys Val Cys Gly Pro Asn Gly Phe Cys
            20                  25                  30

Gly Ser Glu Asn Leu Tyr Phe Gln Gly Arg Gly Thr Gln Ala Glu Glu
        35                  40                  45

Ser Pro Phe Val Gly Asn Pro Gly Asn Ile Thr Gly Ala Arg Gly Leu
    50                  55                  60
```

```
Thr Gly Thr Leu Arg Cys Gln Leu Gln Val Gln Gly Glu Pro Pro Glu
 65                  70                  75                  80

Val His Trp Leu Arg Asp Gly Gln Ile Leu Glu Leu Ala Asp Ser Thr
                 85                  90                  95

Gln Thr Gln Val Pro Leu Gly Glu Asp Glu Gln Asp Asp Trp Ile Val
            100                 105                 110

Val Ser Gln Leu Arg Ile Thr Ser Leu Gln Leu Ser Asp Thr Gly Gln
        115                 120                 125

Tyr Gln Cys Leu Val Phe Leu Gly His Gln Thr Phe Val Ser Gln Pro
    130                 135                 140

Gly Tyr Val Gly Leu Glu Gly Leu Pro
145                 150
```

<210> SEQ ID NO 65
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Ala Pro Arg Gly Thr Gln Ala Glu Glu Ser Pro Phe Val Gly Asn Pro
1               5                  10                  15

Gly Asn Ile Thr Gly Ala Arg Gly Leu Thr Gly Thr Leu Arg Cys Gln
             20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
    50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                 85                  90                  95

Gly His Gln Thr Phe Val Ser Gln Pro Gly Tyr Val Gly Leu Glu Gly
            100                 105                 110

Leu Pro Glu Asn Leu Tyr Phe Gln Gly Gly Cys Pro Gln Gly Arg Gly
        115                 120                 125

Asp Trp Ala Pro Thr Ser Cys Lys Gln Asp Ser Asp Cys Leu Ala Gly
    130                 135                 140

Cys Val Cys Gly Pro Asn Gly Phe Cys Gly Ser
145                 150                 155
```

<210> SEQ ID NO 66
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Asp Tyr Lys Asp Asp Asp Asp Lys Pro Arg Gly Cys Val Arg Leu His
1               5                  10                  15

Glu Ser Cys Leu Gly Gln Gln Val Pro Cys Cys Asp Pro Ala Ala Thr
             20                  25                  30

Cys Tyr Cys Ser Gly Arg Gly Asp Asn Asp Leu Val Cys Tyr Cys Arg
             35                  40                  45
```

Tyr Ala Glu Gly Gln Gly Lys Arg Arg Asn Thr Ile His Glu Phe Lys
 50                  55                  60

Lys Ser Ala Lys Thr Thr Leu Ile Lys Ile Asp Pro Ala Leu Arg Ile
 65                  70                  75                  80

Lys Thr Glu Lys Ala Asn Thr Ala Asp Gln Cys Ala Asn Arg Cys Thr
                 85                  90                  95

Arg Ser Lys Gly Leu Pro Phe Thr Cys Lys Ala Phe Val Phe Asp Lys
             100                 105                 110

Ala Arg Lys Arg Cys Leu Trp Phe Pro Phe Asn Ser Met Ser Ser Gly
         115                 120                 125

Val Lys Lys Glu Phe Gly His Glu Phe Asp Leu Tyr Glu Asn Lys Ala
130                 135                 140

Tyr Ile Arg Asp Cys Ile Ile Gly Arg Gly Arg Asn Tyr Arg Gly Thr
145                 150                 155                 160

Val Ser Ile Thr Lys Ser Gly Ile Lys Cys Gln Pro Trp Ser Ala Met
                165                 170                 175

Ile Pro His Glu His Ser Phe Leu Pro Ser Ser Tyr Arg Gly Glu Asp
            180                 185                 190

Leu Arg Glu Asn Tyr Cys Arg Asn Pro Arg Gly Glu Glu Gly Gly Pro
        195                 200                 205

Trp Cys Tyr Thr Ser Asp Pro Glu Val Arg Tyr Glu Val Cys Asp Ile
210                 215                 220

Pro Gln Cys Ser Glu Val Glu Thr Arg His His His His His His
225                 230                 235

<210> SEQ ID NO 67
<211> LENGTH: 75
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other

<400> SEQUENCE: 67
ggttctgcta gcggttgtnn snnsnnsnns nnsnnsnnst gtaaacaaga ttctgattgt    60
ttggctggtt gtgtt                                                    75

<210> SEQ ID NO 68
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 68
ggttctgcta gcggttgtnn snnsnnsnns nnsnnsnnsn nstgtaaaca agattctgat    60
tgtttggctg gttgtgtt                                                 78

<210> SEQ ID NO 69
<211> LENGTH: 81
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other

<400> SEQUENCE: 69
ggttctgcta gcggttgtnn snnsnnsnns nnsnnsnnsn nsnnstgtaa acaagattct     60
gattgtttgg ctggttgtgt t                                              81

<210> SEQ ID NO 70
<211> LENGTH: 84
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other

<400> SEQUENCE: 70
ggttctgcta gcggttgtnn snnsnnsnns nnsnnsnnsn nsnnsnnstg taaacaagat     60
tctgattgtt tggctggttg tgtt                                            84

<210> SEQ ID NO 71
<211> LENGTH: 62
<212> TYPE: DNA
<213> ORGANISM: Artificial Sequence -continued

```
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other

<400> SEQUENCE: 71
cgtgcccctg agaccacasn nsnnsnnsnn snnsnnacaa acacaaccag ccaaacaatc      60
ag                                                                    62

<210> SEQ ID NO 72
<211> LENGTH: 65
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other

<400> SEQUENCE: 72
cgtgcccctg agaccacasn nsnnsnnsnn snnsnnsnna caaacacaac cagccaaaca      60
atcag                                                                 65

<210> SEQ ID NO 73
```

```
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: modified_base
<222> LOCATION: (41)..(42)
<223> OTHER INFORMATION: a, c, t, g, unknown or other

<400> SEQUENCE: 73
cgtgcccctg agaccacasn nsnnsnnsnn snnsnnsnns nnacaaacac aaccagccaa    60
acaatcag                                                            68

<210> SEQ ID NO 74
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttccctgggt tgcccacgaa gggactttct tcagcctgcg tgcccctgct accaca       56

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggtggttctg gtggtggtgg ttctggtggt ggtggttctg ctagcggttg t            51

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 76

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
                20                  25                  30

Leu Arg Cys Tyr Cys Arg
            35

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 77

His His His His His His
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Gly Ser
1

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Gly Gly Gly Ser Gly Gly Gly Ser Gly Gly Gly Gly Ser
1               5                   10                  15

<210> SEQ ID NO 80
<211> LENGTH: 7
<212> TYPE: PRT
<213> ORGANISM: Tobacco etch virus

<400> SEQUENCE: 80

Glu Asn Leu Tyr Phe Gln Gly
1               5

<210> SEQ ID NO 81
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(12)
<223> OTHER INFORMATION: Any amino acid and this region may be 7-10
      residues in length
<220> FEATURE:

```
<221> NAME/KEY: MOD_RES
<222> LOCATION: (26)..(33)
<223> OTHER INFORMATION: Any amino acid and this region may be 6-8
      residues in length

<400> SEQUENCE: 81

Gly Cys Xaa Xaa Xaa Xaa Xaa Xaa Xaa Xaa Cys Lys Gln Asp
1               5                   10                  15

Ser Asp Cys Leu Ala Gly Cys Val Cys Xaa Xaa Xaa Xaa Xaa
            20                  25                  30

Xaa Cys Gly Arg Gly Thr Gln Ala Glu
        35                  40

<210> SEQ ID NO 82
<211> LENGTH: 8
<212> TYPE: PRT
<213> ORGANISM: Tobacco etch virus

<400> SEQUENCE: 82

Gly Glu Asn Leu Tyr Phe Gln Gly
1               5

<210> SEQ ID NO 83
<211> LENGTH: 233
<212> TYPE: PRT
<213> ORGANISM: mouse

<400> SEQUENCE: 83

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
                20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
        50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

```
<210> SEQ ID NO 84
<211> LENGTH: 146
<212> TYPE: PRT
<213> ORGANISM: Artifical sequence
<220> FEATURE:
<223> OTHER INFORMATION: Synthetic polypeptide

<400> SEQUENCE: 84

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
                20                  25                  30

Gly Ser Arg Gly Thr Gln Ala Glu Glu Ser Pro Phe Val Gly Asn Pro
            35                  40                  45

Gly Asn Ile Thr Gly Ala Arg Gly Leu Thr Gly Thr Leu Arg Cys Gln
        50                  55                  60

Leu Gln Val Gln Gly Glu Pro Pro Glu Val His Trp Leu Arg Asp Gly
65                  70                  75                  80

Gln Ile Leu Glu Leu Ala Asp Ser Thr Gln Thr Gln Val Pro Leu Gly
                85                  90                  95

Glu Asp Glu Gln Asp Asp Trp Ile Val Val Ser Gln Leu Arg Ile Thr
            100                 105                 110

Ser Leu Gln Leu Ser Asp Thr Gly Gln Tyr Gln Cys Leu Val Phe Leu
        115                 120                 125

Gly His Gln Thr Phe Val Ser Gln Pro Gly Tyr Val Gly Leu Glu Gly
    130                 135                 140

Leu Pro
145

<210> SEQ ID NO 85
<211> LENGTH: 239
<212> TYPE: PRT
<213> ORGANISM: Artifical sequence
<220> FEATURE:
<223> OTHER INFORMATION: Synthetic polypeptide

<400> SEQUENCE: 85

Asp Tyr Lys Asp Asp Asp Asp Lys Pro Arg Gly Cys Val Arg Leu His
1               5                   10                  15

Glu Ser Cys Leu Gly Gln Gln Val Pro Cys Cys Asp Pro Ala Ala Thr
                20                  25                  30

Cys Tyr Cys Ser Gly Arg Gly Asp Asn Asp Leu Val Cys Tyr Cys Arg
            35                  40                  45

Tyr Ala Glu Gly Gln Arg Lys Arg Arg Asn Thr Ile His Glu Phe Lys
        50                  55                  60

Lys Ser Ala Lys Thr Thr Leu Ile Lys Ile Asp Pro Ala Leu Lys Ile
65                  70                  75                  80

Lys Thr Glu Lys Val Asn Thr Ala Asp Gln Cys Ala Asn Arg Cys Thr
                85                  90                  95

Arg Asn Lys Gly Leu Pro Phe Thr Cys Lys Ala Phe Val Phe Asp Lys
            100                 105                 110

Ala Arg Lys Arg Cys Leu Trp Phe Pro Phe Asn Ser Met Ser Ser Gly
        115                 120                 125

Val Lys Lys Glu Phe Gly His Glu Phe Asp Leu Tyr Glu Asn Lys Asp
    130                 135                 140

Tyr Ile Arg Asp Cys Ile Ile Gly Asn Gly Arg Ser Tyr Arg Gly Thr
```

```
145                 150                 155                 160

Val Ser Ile Thr Lys Ser Gly Ile Lys Cys Gln Pro Trp Ser Ser Met
                165                 170                 175

Ile Pro His Glu His Ser Phe Leu Pro Ser Ser Tyr Arg Gly Glu Asp
            180                 185                 190

Leu Arg Glu Asn Tyr Cys Arg Asn Pro Arg Gly Glu Glu Gly Gly Pro
        195                 200                 205

Trp Cys Phe Thr Ser Asp Pro Glu Val Arg Tyr Glu Val Cys Asp Ile
    210                 215                 220

Pro Gln Cys Ser Glu Val Glu Thr Arg His His His His His His
225                 230                 235

<210> SEQ ID NO 86
<211> LENGTH: 239
<212> TYPE: PRT
<213> ORGANISM: Artifical sequence
<220> FEATURE:
<223> OTHER INFORMATION: Synthetic polypeptide

<400> SEQUENCE: 86

Asp Tyr Lys Asp Asp Asp Lys Pro Arg Gly Cys Val Arg Leu His
1               5                   10                  15

Glu Ser Cys Leu Gly Gln Gln Val Pro Cys Cys Asp Pro Ala Ala Thr
            20                  25                  30

Cys Tyr Cys Ser Gly Arg Gly Asp Asn Asp Leu Val Cys Tyr Cys Arg
        35                  40                  45

Tyr Ala Glu Gly Gln Arg Lys Arg Arg Asn Thr Ile His Glu Phe Lys
    50                  55                  60

Lys Ser Ala Lys Thr Thr Leu Ile Lys Ile Asp Pro Ala Leu Lys Ile
65                  70                  75                  80

Lys Thr Glu Lys Val Asn Thr Ala Asp Gln Cys Ala Asn Arg Cys Thr
                85                  90                  95

Arg Asn Lys Gly Leu Pro Phe Thr Cys Lys Ala Phe Val Phe Asp Lys
            100                 105                 110

Ala Arg Lys Arg Cys Leu Trp Phe Pro Phe Asn Ser Met Ser Ser Gly
        115                 120                 125

Val Lys Lys Glu Phe Gly His Glu Phe Asp Leu Tyr Glu Asn Lys Asp
    130                 135                 140

Tyr Ile Arg Ala Cys Ile Ile Gly Asn Gly Arg Ser Tyr Arg Gly Thr
145                 150                 155                 160

Val Ser Ile Thr Lys Ser Gly Ile Lys Cys Gln Pro Trp Ser Ser Met
                165                 170                 175

Ile Pro His Glu His Ser Phe Leu Pro Ser Ser Tyr Arg Gly Glu Asp
            180                 185                 190

Leu Arg Glu Asn Tyr Cys Arg Asn Pro Arg Gly Glu Glu Gly Gly Pro
        195                 200                 205

Trp Cys Phe Thr Ser Asp Pro Glu Val Arg Tyr Glu Val Cys Asp Ile
    210                 215                 220

Pro Gln Cys Ser Glu Val Glu Thr Arg His His His His His His
225                 230                 235

<210> SEQ ID NO 87
<211> LENGTH: 234
<212> TYPE: PRT
<213> ORGANISM: Artificial Sequence
<220> FEATURE:
<223> OTHER INFORMATION: Synthetic polypeptide
```

<400> SEQUENCE: 87

```
Asp Tyr Lys Asp Asp Asp Lys Pro Arg Gly Cys Pro Arg Pro Arg
1               5                   10                  15

Gly Asp Asn Pro Pro Leu Thr Cys Ser Gln Asp Ser Asp Cys Leu Ala
            20                  25                  30

Gly Cys Val Cys Gly Pro Asn Gly Phe Cys Gly Tyr Ala Glu Gly Gln
        35                  40                  45

Gly Lys Arg Arg Asn Thr Ile His Glu Phe Lys Lys Ser Ala Lys Thr
    50                  55                  60

Thr Leu Ile Lys Ile Asp Pro Ala Leu Arg Ile Lys Thr Glu Lys Ala
65                  70                  75                  80

Asn Thr Ala Asp Gln Cys Ala Asn Arg Cys Thr Arg Ser Lys Gly Leu
                85                  90                  95

Pro Phe Thr Cys Lys Ala Phe Val Phe Asp Lys Ala Arg Lys Arg Cys
            100                 105                 110

Leu Trp Phe Pro Phe Asn Ser Met Ser Ser Gly Val Lys Lys Glu Phe
        115                 120                 125

Gly His Glu Phe Asp Leu Tyr Glu Asn Lys Ala Tyr Ile Arg Asp Cys
    130                 135                 140

Ile Ile Gly Arg Gly Arg Asn Tyr Arg Gly Thr Val Ser Ile Thr Lys
145                 150                 155                 160

Ser Gly Ile Lys Cys Gln Pro Trp Ser Ala Met Ile Pro His Glu His
                165                 170                 175

Ser Phe Leu Pro Ser Ser Tyr Arg Gly Glu Asp Leu Arg Glu Asn Tyr
            180                 185                 190

Cys Arg Asn Pro Arg Gly Glu Glu Gly Gly Pro Trp Cys Tyr Thr Ser
        195                 200                 205

Asp Pro Glu Val Arg Tyr Glu Val Cys Asp Ile Pro Gln Cys Ser Glu
    210                 215                 220

Val Glu Thr Arg His His His His His His
225                 230
```

<210> SEQ ID NO 88
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 88

```
Asp Tyr Lys Asp Asp Asp Lys Pro Arg Gly Cys Pro Arg Pro Arg
1               5                   10                  15

Gly Asp Asn Pro Pro Leu Thr Cys Ser Gln Asp Ser Asp Cys Leu Ala
            20                  25                  30

Gly Cys Val Cys Gly Pro Asn Gly Phe Cys Gly Tyr Ala Glu Gly Gln
        35                  40                  45

Arg Lys Arg Arg Asn Thr Ile His Glu Phe Lys Lys Ser Ala Lys Thr
    50                  55                  60

Thr Leu Ile Lys Ile Asp Pro Ala Leu Lys Ile Lys Thr Glu Lys Val
65                  70                  75                  80

Asn Thr Ala Asp Gln Cys Ala Asn Arg Cys Thr Arg Asn Lys Gly Leu
                85                  90                  95

Pro Phe Thr Cys Lys Ala Phe Val Phe Asp Lys Ala Arg Lys Arg Cys
            100                 105                 110
```

```
Leu Trp Phe Pro Phe Asn Ser Met Ser Ser Gly Val Lys Lys Glu Phe
            115                 120                 125

Gly His Glu Phe Asp Leu Tyr Glu Asn Lys Asp Tyr Ile Arg Asp Cys
        130                 135                 140

Ile Ile Gly Asn Gly Arg Ser Tyr Arg Gly Thr Val Ser Ile Thr Lys
145                 150                 155                 160

Ser Gly Ile Lys Cys Gln Pro Trp Ser Ser Met Ile Pro His Glu His
                165                 170                 175

Ser Phe Leu Pro Ser Ser Tyr Arg Gly Glu Asp Leu Arg Glu Asn Tyr
                180                 185                 190

Cys Arg Asn Pro Arg Gly Glu Glu Gly Gly Pro Trp Cys Phe Thr Ser
        195                 200                 205

Asp Pro Glu Val Arg Tyr Glu Val Cys Asp Ile Pro Gln Cys Ser Glu
    210                 215                 220

Val Glu Thr Arg His His His His His His
225                 230

<210> SEQ ID NO 89
<211> LENGTH: 234
<212> TYPE: PRT
<213> ORGANISM: artifcial sequence
<220> FEATURE:
<223> OTHER INFORMATION: Synthetic polypeptide

<400> SEQUENCE: 89

Asp Tyr Lys Asp Asp Asp Lys Pro Arg Gly Cys Pro Arg Pro Arg
1               5                   10                  15

Gly Asp Asn Pro Pro Leu Thr Cys Ser Gln Asp Ser Asp Cys Leu Ala
                20                  25                  30

Gly Cys Val Cys Gly Pro Asn Gly Phe Cys Gly Tyr Ala Glu Gly Gln
            35                  40                  45

Arg Lys Arg Arg Asn Thr Ile His Glu Phe Lys Lys Ser Ala Lys Thr
        50                  55                  60

Thr Leu Ile Lys Ile Asp Pro Ala Leu Lys Ile Lys Thr Glu Lys Val
65                  70                  75                  80

Asn Thr Ala Asp Gln Cys Ala Asn Arg Cys Thr Arg Asn Lys Gly Leu
                85                  90                  95

Pro Phe Thr Cys Lys Ala Phe Val Phe Asp Lys Ala Arg Lys Arg Cys
            100                 105                 110

Leu Trp Phe Pro Phe Asn Ser Met Ser Ser Gly Val Lys Lys Glu Phe
        115                 120                 125

Gly His Glu Phe Asp Leu Tyr Glu Asn Lys Asp Tyr Ile Arg Ala Cys
        130                 135                 140

Ile Ile Gly Asn Gly Arg Ser Tyr Arg Gly Thr Val Ser Ile Thr Lys
145                 150                 155                 160

Ser Gly Ile Lys Cys Gln Pro Trp Ser Ser Met Ile Pro His Glu His
                165                 170                 175

Ser Phe Leu Pro Ser Ser Tyr Arg Gly Glu Asp Leu Arg Glu Asn Tyr
                180                 185                 190

Cys Arg Asn Pro Arg Gly Glu Glu Gly Gly Pro Trp Cys Phe Thr Ser
        195                 200                 205

Asp Pro Glu Val Arg Tyr Glu Val Cys Asp Ile Pro Gln Cys Ser Glu
    210                 215                 220

Val Glu Thr Arg His His His His His His
225                 230
```

FUSION PROTEINS COMPRISING AN ENGINEERED KNOTTIN PEPTIDE AND USES THEREOF

CROSS-REFERENCE TO RELATED APPLICATIONS

This application claims priority from U.S. Provisional Patent Application No. 61/411,350 filed on Nov. 8, 2010, which is hereby incorporated by reference in its entirety and is a U.S. national stage application of PCT/US2011/059599, which is also incorporated herein by reference in its entirety.

STATEMENT OF GOVERNMENTAL SUPPORT

This invention was made with Government support under contracts CA151706, CA131706, and CA104706, awarded by the National Institutes of Health. The Government has certain rights in this invention.

REFERENCE TO SEQUENCE LISTING

The instant application contains a Sequence Listing which has been submitted in ASCII format via EFS-Web and is hereby incorporated by reference in its entirety. The sequence listing was created May 1, 2013, has 61,262 bytes and is named "381593pct.txt".

BACKGROUND OF THE INVENTION

Field of the Invention

The present invention relates to the field of protein engineering, and to the field of knottin peptides, i.e. peptides with particularly well-defined scaffolds and high stability, also referred to as cystine knot miniproteins in the art.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Protein-protein interactions mediate nearly every process in living systems and gene duplication and recombination is believed to be critical to the evolution of protein function. Directed evolution is an invaluable tool for optimizing proteins, however, in vitro evolution strategies generally focus on directly engineering the active site or binding site of the protein of interest. There are limited examples harnessing the power of gene duplication and combination in the directed evolution of protein function.

Specific molecular recognition events define the interactions between ligands and receptors in living systems. These interactions mediate a host of biological processes, highlighting the importance of molecular recognition in many physiological processes. Engineering molecular recognition has been widely used in the biotechnology arena to develop protein-based biosensors, imaging agents, and therapeutics candidates. Traditional approaches for engineering enhanced recognition focus on optimizing the specific interaction, for example enhancing antibody recognition or affinity maturation of native protein-protein interactions. In nature, however, molecular recognition often occurs at the interface of multiple domains, and the linkage of protein domains through gene recombination is believed to play a strong role in the evolution of protein function. There are few instances in the literature of this approach being used to engineer protein function in vitro. Examples that do exist are limited to either evolving a completely synthetic interaction or optimizing a protein-peptide interaction. In the same way that traditional directed evolution studies have provided insights into the natural evolution of proteins, harnessing nature's approach of domain addition and evolution would provide new avenues to explore natural evolution pathways. Further analysis of domain addition and evolution, focusing on enhancing an existing high affinity protein-protein interaction, would provide a rigorous test of the utility of this approach for the study of molecular recognition and for use as a protein engineering tool.

SPECIFIC PATENTS AND PUBLICATIONS

Knottins are described in the knottin database, http(colon slash slash) knottin.cbs.cnrs.fr/Knottins.php, which provides sequences and structures of various knottin peptides.

U.S. Pat. No. 7,674,881 to Kent, et al., issued Mar. 9, 2010, entitled "Convergent synthesis of proteins by kinetically controlled ligation," describes the synthesis of EETI-II.

Liu U.S. Pat. No. 5,468,634, entitled "Axl oncogene", discloses isolated DNA sequences encoding a mammalian axl receptor which exhibits axl oncogene activity.

US 2009/0257952 to Cochran et al., published Oct. 15, 2009, entitled "Engineered Integrin Binding Peptides," discloses engineered peptides that bind with high affinity (low equilibrium dissociation constant ($K_D$)) to the cell surface receptors of fibronectin (alpha 5 beta1 integrin) or vitronectin (alpha v beta 3 and alpha v beta 5 integrins).

BRIEF SUMMARY OF THE INVENTION

The following brief summary is not intended to include all features and aspects of the present invention, nor does it imply that the invention must include all features and aspects discussed in this summary. For the sake of brevity, it is to be understood that certain features of different embodiments may be combined. even though such alternative combinations or subcombinations are not explicitly recited.

Thus, in certain aspects, the present invention comprises (a) a knottin polypeptide having therein a binding loop for binding to a first target; and (b) a second polypeptide having therein a sequence for binding to a second target, said second polypeptide being either (i) a cell surface receptor binding to said second target or (ii) a cell surface receptor ligand, binding to said second target. As is known in knottins, binding loops are typically between constrained cysteine residues. These loops may be altered by preparing a library of randomized sequences. In this aspect, the knottin polypeptide contains a non-native sequence in its binding loop. That is, the sequence is not normally present in the knottin; preferably it has been selected by a screening procedure for high binding. In certain aspects of the invention, the fusion protein will contain a non-native sequence mediates attachment between a cell and the tissues surrounding it. In certain aspects of the invention, the knottin polypeptide contains a sequence that mediates binding to one or more of (a) alpha v beta 3 integrin, (b) and alpha v beta 5 integrin, and (c) alpha 5 beta 1 integrin. In certain aspects of the invention, the fusion protein comprises a second polypeptide which is an extracellular domain of a receptor tyrosine kinase. In certain aspects of the invention, the second polypeptide is a receptor tyrosine kinase Ig1 domain. In certain aspects of the invention, the Ig1 domain is from Axl. MuSK, or the FGF receptor. In certain aspects of the invention, the receptor tyrosine kinase is an Axl receptor. In certain aspects of the invention, the knottin polypeptide is selected from the group consisting of EETI-II AgRP, and agatoxin. In certain aspects of the invention, the fusion protein has a binding loop domain is engineered to bind to one of $\alpha 5\beta 1$ integrin, $\alpha v\beta 3$ integrin, or $\alpha v\beta 5$ integrin.

In certain aspects of the invention, the fusion protein comprises (a) an EETI-II or AgRP knottin polypeptide comprising a binding loop with high affinity to an integrin; and (b) a polypeptide selected from the group consisting of (i) an Axl extracellular domain and (ii) NK1 fragment of hepatocyte growth factor.

Certain aspects of the invention comprise a method for preparing a fusion protein, comprising the steps of: (a) preparing a library having a number of DNA constructs encoding the fusion protein and a number of randomized DNA sequences within the DNA constructs; (b) expressing the DNA constructs in the library in yeast, wherein expressed DNA constructs are displayed as polypeptides with randomized sequences on the yeast surface; (c) screening the clones for binding of the expressed DNA constructs to the first target or the second target by contacting the clones with a target; (d) selecting clones that express translated DNA constructs that bind with high affinity to the target; and (e) obtaining the coding sequences of the selected clones, whereby said fusion protein may be prepared.

Certain accepts of the invention comprise a method for inhibiting binding of a ligand to a receptor, comprising the steps of: (a) administering an amount of a soluble fusion protein comprising (i) a polypeptide encoding an extracellular domain of a receptor to be inhibited and (ii) a knottin polypeptide having a loop domain engineered to bind to a cell surface receptor that is not the receptor to be inhibited.

In certain aspects of the various methods, the tyrosine kinase may be a TAM receptor tyrosine kinase.

In certain aspects, the present invention comprises a method for preparing a bispecific, or multispecific, fusion protein that contains an engineered knottin portion and another binding portion that, preferably, is a receptor, receptor ligand, or a fragment thereof having the binding property of the native molecule. The fusion protein thus prepared has two different binding portions, and two separate ligands. The knottin portion is fused at its C-terminus to the N terminus of the binding portion. Alternatively, it may be fused at its N terminus to the C terminus of the binding portion.

In certain aspects, the present invention comprises a method for preparing a fusion protein comprising a first polypeptide that binds to a first binding partner (e.g. a receptor or receptor ligand) fused to a second polypeptide (e.g. a knottin) having a loop domain engineered to bind with high affinity to a second binding partner, comprising the steps of: (a) preparing a library having a number of DNA constructs encoding the fusion protein and a number of randomized loop domains, wherein the library provides a degree of variation of binding and a number of tight binders to be selected from the library; (b) expressing the DNA constructs in the library as protein variants; (c) screening the library for binding of the protein variants to the second binding partner, (d) selecting clones that express DNA constructs that bind with high affinity to the second binding partner, and (e) obtaining the coding sequences of the selected clones, whereby said fusion protein may be prepared. The second binding partner selected may be an entirely different molecule (protein, glycoprotein, polysaccharide, lipid, cell structure, viral epitope etc.) or it may be a different epitope on the binding site for the first binding partner (receptor or receptor ligand). In certain aspects, the present invention utilizes a first polypeptide that is a receptor fragment. For example, a cell surface receptor having various domains is used in the form of a fragment encoding an extracellular ligand binding domain. The cell surface receptor may be a receptor tyrosine kinase. In certain aspects of the invention, the first polypeptide may be a receptor ligand, or a fragment of such a ligand that binds to a receptor. The ligand may be an agonist or an antagonist. The first polypeptide may have a sequence which is at least a portion of a sequence selected from the group consisting of Axl, c-Met, HGF, VEGF, VEGF receptor, and Gas6.

In certain aspects of the present invention, the second polypeptide is a knottin scaffold and may be selected from the group consisting of EETI-II, AgRP, and agatoxin. It is also contemplated that the knottin scaffold may be $\omega$-conotoxin. In certain aspects of the present invention, the knottin loop domain is engineered to bind to an integrin. In certain aspects of the present invention, the method comprises cloning a random yeast display library having loop portions that are selected for binding to the target of interest.

In certain aspects, the present invention comprises a fusion protein comprising a receptor ligand polypeptide, said receptor ligand binding to a receptor at a specific receptor binding site, fused to a knottin polypeptide having a loop domain engineered to bind with high affinity to a binding partner that is not the specific receptor binding site for the receptor ligand. In certain aspects of the present invention, the receptor ligand polypeptide is a fragment of a native ligand. In certain aspects of the present invention, the fusion protein comprises a fragment that is a fragment of a growth factor, such as an NK1 fragment of hepatocyte growth factor, which consists of the HGF amino terminus through the first kringle domain.

Certain aspects of the present invention comprise a fusion protein comprising a receptor polypeptide, said receptor binding to a ligand at a specific ligand binding site, fused to a knottin polypeptide having a loop domain engineered to bind with high affinity to a binding partner that is not the specific ligand binding site. The receptor may be a receptor tyrosine kinase. The receptor tyrosine kinase may be selected from the group consisting of Axl, a receptor tyrosine kinase involved in solid tumor progression and MET, which is the hepatocyte growth factor receptor. It may include closely receptor tyrosine kinases closely related to Axl, such as Tyro-3 and Mer.

In certain aspects of the present invention the fusion protein comprises a knottin polypeptide selected from the group consisting of EETI-II, AgRP, and agatoxin. In certain aspects of the present invention, the fusion protein comprises a loop domain engineered to bind to one of $\alpha_5\beta_1$ integrin, $\alpha_v\beta_3$ integrin, or $\alpha_v\beta_5$ integrin. In certain aspects of the present invention, the loop domain is engineered to bind to $\alpha_3$ integrin. In certain aspects of the present invention, the loop domain is engineered to bind to an $\alpha_v$ or $\beta_3$ integrin subunit.

BRIEF DESCRIPTION OF THE DRAWINGS

FIG. 1D is a representation of the EETI-II-axl fusion library creation and the screening to obtain fusions EA 7.01, 7.03, 7.05, 8.04 and 8.05. Both loops 1 and 2 can be seen to be randomized; only a portion of the Axl1 Ig1 sequence is represented. The sequences are truncated due to the length of the Axl Ig1 portion.

DETAILED DESCRIPTION OF THE PREFERRED EMBODIMENTS

Overview

The present invention comprises the creation of novel fusion proteins that include an engineered knottin peptide fused to a second, different peptide or protein which provides a different binding function. The second polypeptide is a receptor or a receptor ligand. Preferably, a portion of the knottin peptide is replaced with a sequence that has been created for binding to an integrin. In addition, the fusion proteins may comprise a knottin peptide fused to another protein where the other protein facilitates proper expression and folding of the knottin.

The present invention may be used to enhance receptor ligand binding. Native proteins involved in ligand-receptor interactions are promising starting points for engineering therapeutic candidates. Traditional approaches to engineering protein-protein interactions have focused on optimizing an existing interaction. In nature, however, protein-protein interactions often occur at the junction of multiple domains and gene recombination plays a strong role in the evolution of protein function. Using these observations, we have developed a general approach to engineering existing protein-protein interactions we refer to as "domain addition and evolution" in which enhancement is accomplished by expanding the binding interface through the addition and subsequent in vitro evolution of a synthetic binding domain.

Figure 1A:
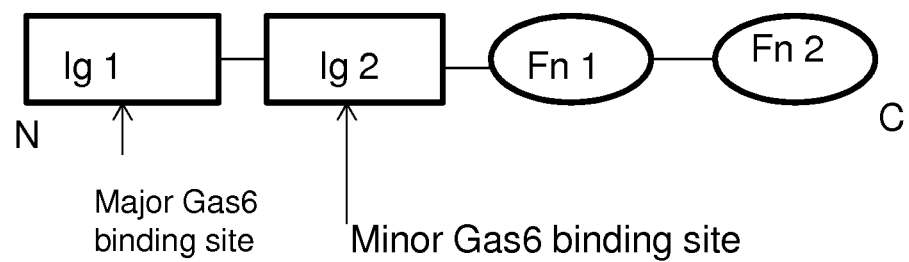
FIG. 1A is a schematic drawing of the Axl extracellular domain.
Figure 1B:
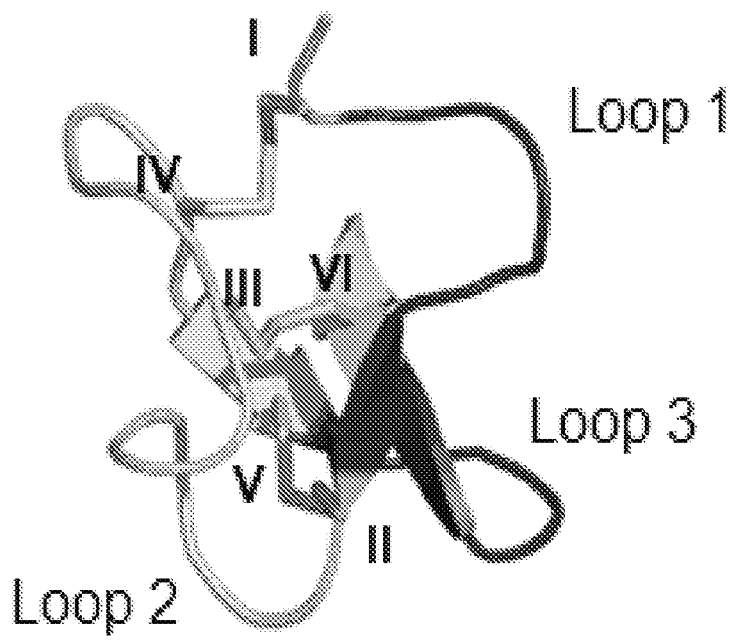
FIG. 1B is a ribbon rendering of an EETI-II crystal structure.
Figure 1C:
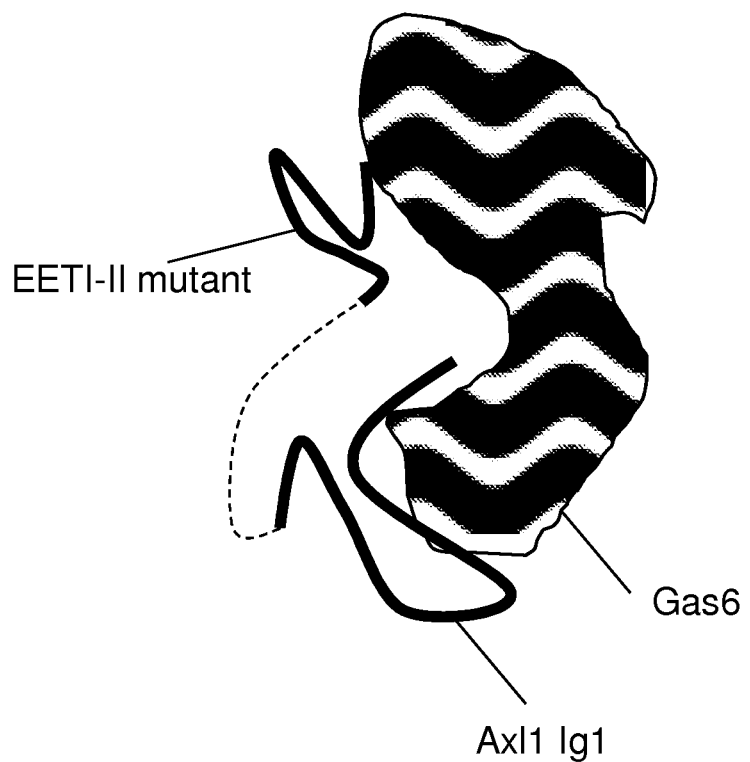
FIG. 1C is a schematic drawing of the Axl-EETI-II fusion bound to the Gas6 ligand.

FIG. 1 shows that the present fusions in effect add another epitope for receptor-ligand binding. FIG. 1A shows that the Axl extracellular domain contains two immunoglobulin-like domains (Ig1 and Ig2), followed by two fibronectin type-III like (Fn) domains. FIG. 1B shows EETI-II crystal structure (PDB ID: 2ETI). Loops 1 and 3, which were randomized for domain addition and evolution library, are shown in black. Cysteines I-VI are noted. FIG. 1C is a schematic showing domain addition strategy. EETI-II mutant library is linked to the N-terminus of Axl Ig1 (black ribbons to the bottom left of the structure) to screen for EETI-II mutants that bind to an adjacent epitope on the Gas6 ligand. Axl-Gas6 structure adapted from PDB ID: 2C5D. FIG. 1D shows a listing of amino acid sequences that show the EETI-II loop 1 and loop 3 regions that were randomized and the fusion to the Axl Ig1 domain. Figure was generated using PyMol.

Figure 2A:
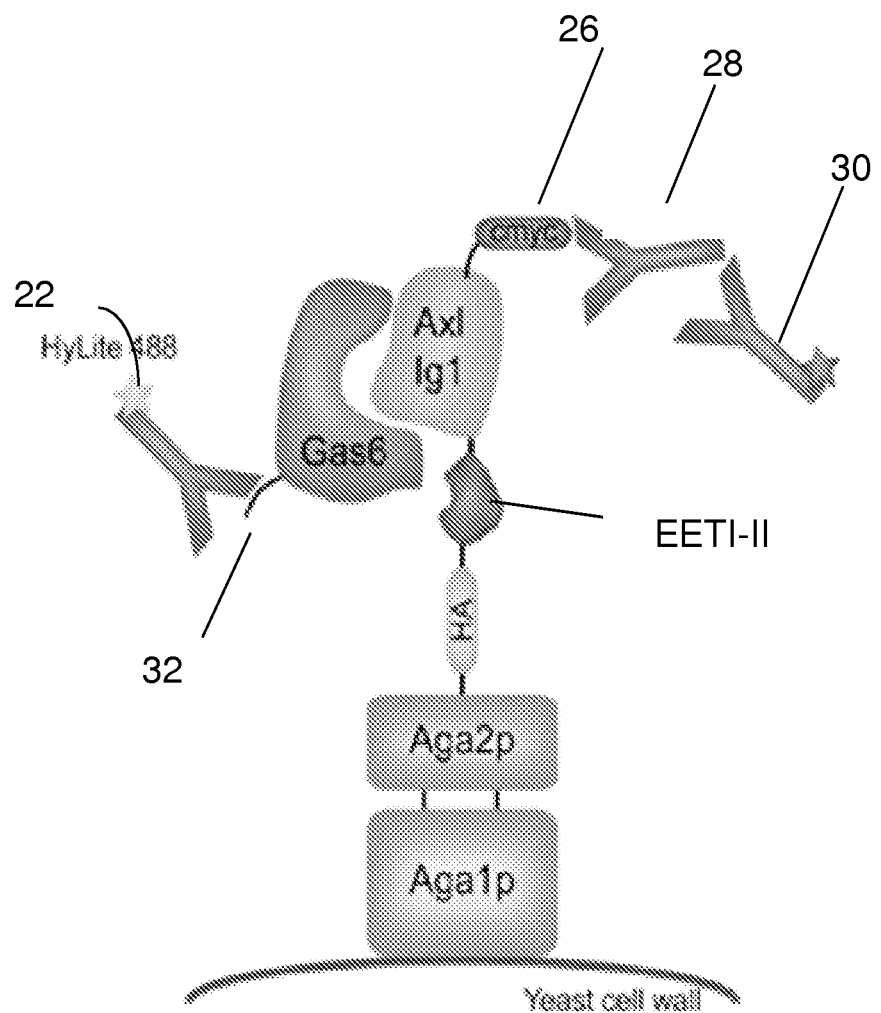
FIG. 2A is a schematic drawing of the yeast display construct.
Figure 2B:
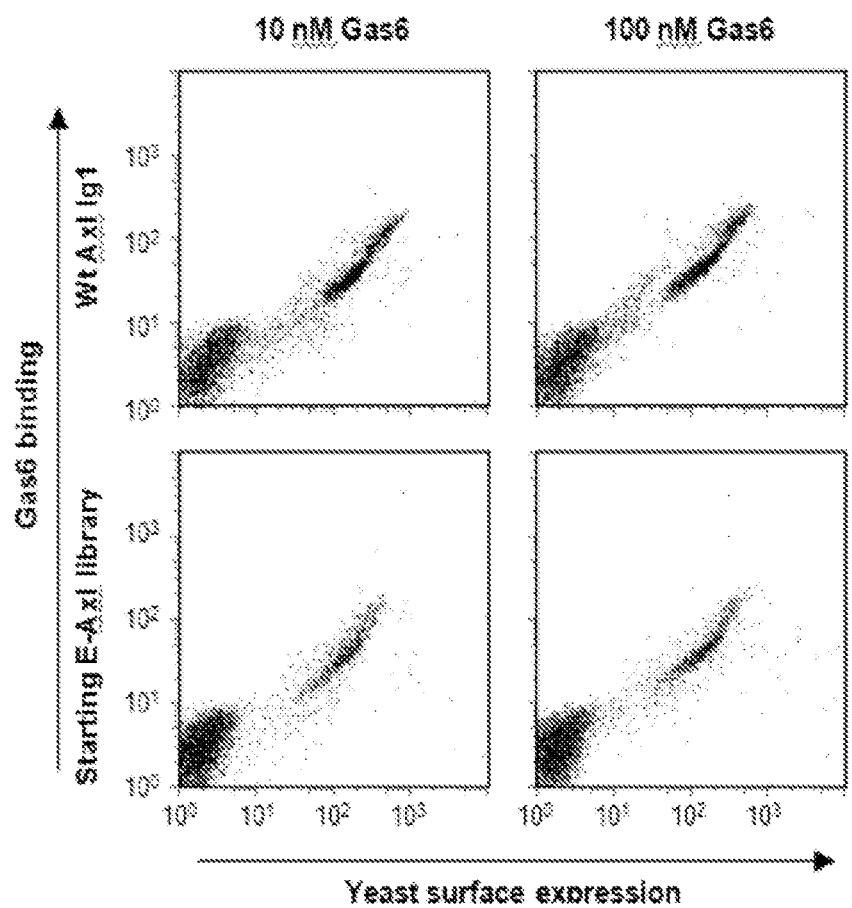
FIG. 2B is a set of scatter plots showing comparison of binding by wild-type Axl Ig1 and the starting E-Axl library

FIGS. 2A and 2B shows the yeast display construct and evaluation of starting E-Axl library EETI-II mutants (randomized loops) linked to Axl. (2A) Yeast-displayed E-Axl construct. The protein of interest is expressed as a genetic fusion to the yeast Aga2 protein, which is disulfide bonded to the yeast Aga1 protein. The Aga1 protein is covalently linked to the yeast cell wall, thereby tethering the entire display construct to the yeast cell surface. The use of Aga1 and Aga2 proteins in yeast display has been previously described in connection with surface display of antibodies. See, e.g. U.S. Pat. No. 6,423,538 entitled "Yeast cell surface display of proteins and uses thereof." by K. Dane Wittrup et al.

The HA and c-myc epitope tags flanking the protein of interest can be stained for relative yeast surface expression levels using commercially available antibodies (c-myc staining shown for reference). Soluble Gas6 can be used to test binding to the yeast-displayed protein; Gas6 binding is illuminated with a fluorescently labeled antibody against the hexahistidine tag (SEQ ID NO: 77) on Gas6. FIG. 2B presents scatter plots showing comparison of binding by wild-type Axl Ig1 and the starting E-Axl library.

1. Knotting Fusions Having Bispecific or Multispecific Binding

In certain aspects, the present invention comprises fusion proteins that are bispecific or multispecific in that they can bind to and/or inhibit two or more receptors or receptor ligands for increased therapeutic efficacy. These fusions may comprise N-terminal or C-terminal knottins engineered to contain, as one example, an integrin-binding portion. Integrin binding knottins are described in US 2009/0257952 by Cochran et al. entitled "Engineered Integrin Binding Peptides." Engineered peptides that bind with high affinity (low equilibrium dissociation constant ($K_D$)) to the cell surface receptors of fibronectin ($\alpha_5\beta_1$ integrin) or vitronectin ($\alpha_v\beta_3$ and $\alpha_v\beta_5$ integrins) are disclosed. Knottins with novel binding properties may be fused to generate hetero-oligomeric bispecific proteins. This application is incorporated herein by reference, as provided in the concluding paragraph hereof, and may be consulted further for descriptions of integrin-binding knottins. The specific integrin binding partner used here may be specific as to both alpha and beta integrin chains, or only to a beta chain. In the latter case, the integrin binding will be multispecific in that different alpha-beta integrin combinations will exist.

For example, an integrin-binding knottin—ligand fusion has been created using a fragment of a growth factor, NK1. The integrin binding knottin contains a loop that has been engineered to bind specifically to a selected integrin, such as $\alpha_5\beta_1$, $\alpha_v\beta_3$, and $\alpha_v\beta_5$, particularly $\alpha_v\beta_3$ integrins. NK1 is a fragment of the polypeptide growth factor HGF/SF which acts as agonist of the MET receptor. It is described more fully in US 2004/0236073 A1 by Gherardi, entitled "Nk1 fragment of hepatocyte growth factor/scatter factor (hgf/sf) and variants thereof, and their use." Briefly, HGF/SF has a unique domain structure that resembles that of the blood proteinase precursor plasminogen and consists of six domains: an N-terminal (N) domain, homologous to plasminogen activation peptide, four copies of the kringle (K) domain and a catalytically inactive serine proteinase domain. Two products of alternative splicing of the primary HGF/SF transcript encode NK1, a fragment containing the N and the first K domain, K1, and NK2, a fragment containing the N, K1 and second kringle, K2, domains. The sequence may be found in Mol Cell Biol, March 1998, p. 1275-1283, Vol. 18, No. 3.

As another example, an integrin binding knottin—receptor fusion was prepared using Axl. The Axl receptor is described in U.S. Pat. No. 5,468,634 to Liu. Briefly, Axl is a receptor tyrosine kinase with a structure of the extracellular region that juxtaposes IgL and FNIII repeats. It is involved in the stimulation of cell proliferation. It can bind to the vitamin K-dependent protein Gas6, thereby transducing signals into the cytoplasm. The extracellular domain of Axl can be cleaved and a soluble extracellular domain of 65 kDa can be released. Cleavage enhances receptor turnover, and generates a partially activated kinase (O'Bryan J P, Fridell Y W. Koski R, Varnum B. Liu E T. (1995) J Biol Chem. 270(2):551-557). However, the function of the cleaved domain is unknown.

The Axl receptor has two Gas6 binding sites (FIG. 1A): a major, high affinity site located in its Ig1 domain, and a weaker minor site in its Ig2 domain. An active 2:2 signaling complex is formed when Gas6 associates with Axl via its high affinity site, after which association through the weak binding site results in receptor dimerization and activation. This is a therapeutically relevant ligand-receptor system as Axl overexpression results in invasion and metastasis in a range of cancer cell lines and inhibition of Axl signaling suppresses tumor cell migration and metastasis. The bispecific protein generated binds with high affinity to integrins and the Axl ligand Gas6. FIG. 1 shows that the sequences represent an outline of domain addition and evolution library generation and screening: first row shows the wild-type EETI-II sequence with cysteine bonds and loops between cysteines; second row shows loops 1 and 3 where x residues are added; loops 1 and 3 of EETI-TI are randomized to generate the loop library and fused to the N-terminus of Axl Ig1; third row shows sequences of EETI-II-axl fusion mutants EA 7.01, EA 7.06, and EA 8.04; bottom row lists sequences from identification of a PGM, or P-G/T-M/K motif.

The Axl amino acid sequence may be found in NCBI UniGene 26362, and Genbank Accession Number P30530.

In another aspect of the present invention, the receptor or other fusion protein fused to the knottin, is also modified and mutated for binding purposes, in addition to being fused to a knottin that is mutated for binding purposes. This is shown in Example 6. In this embodiment, the receptor, which is to be used as a decoy, is first truncated to an extracellular domain. In the case of Axl, a portion of the signal peptide and a small portion of the extracellular domain (about 110 amino acids from the extracellular domain of about 426 amino acids were used). Using error-prone DNA amplification, mutations are introduced into the DNA sequence encoding the receptor fragment. The resulting clones are screened for binding to the native ligand (Gas6 in the case of Axl), and tighter binders are selected, e.g. by cell sorting. A variety of receptor constructs could be used.

This knottin-Axl fusion can function as a bispecific or multispecific molecule capable of concurrently antagonizing both integrin binding as well as the native Gas6/Axl interactions. Gas6 is a soluble ligand whereas the integrins are cell surface receptors, allowing both targets to be bound at the same time. Binding of Gas6 will sequester the soluble ligand, preventing it from associating with, and subsequently activating endogenous Axl receptor. Binding to integrin receptors will prevent them from binding to extracellular matrix proteins.

The fusion of an integrin-binding peptide to a growth receptor or a signal transducing receptor such as a receptor tyrosine kinase is advantageous in that there is significant cross-talk between integrin and growth factor receptor pathways. For example, strong cross-talk exists between integrins and Met receptor. An agent that targets both receptors will be better at inhibiting angiogenesis and metastasis. Integrin targeting by means of a fusion of a therapeutic protein and an integrin-binding knottin can also localize the second therapeutic agent to the tumor cells, increasing efficacy through avidity effects. Moreover, an imaging agent that can target two tumor receptors would generate an increased signal and can detect smaller tumors for earlier detection.

Knottin-Fc Fusions

Another example (see Example 12) of a fusion protein as described herein is a fusion between an integrin binding knottin and an Fc portion of a mouse antibody. The Fc portion of an antibody is formed by the two carboxy terminal domains of the two heavy chains that make up an immunoglobin molecule. The IgG molecule contains 2 heavy chains (~50 kDa each) and 2 light chains (~25 kDa each). The general structure of all antibodies is very similar, a small region at the tip of the protein is extremely variable, allowing millions of antibodies with slightly different tip structures to exist. This region is known as the hypervariable region (Fab). The other fragment contains no antigen-binding activity but was originally observed to crystallize readily, and for this reason was named the Fc fragment, for Fragment crystallizable. This fragment corresponds to the paired $CH_2$ and $CH_3$ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge. This has been demonstrated by electron microscopy of antibodies bound to haptens. Thus the present fusion proteins can be made to contain two knottin peptides, one on each arm of the antibody fragment.

The Fc portion varies between antibody classes (and subclasses) but is identical within that class. The C-terminal end of the heavy chains form the Fc region. The Fc region plays an important role as a receptor binding portion. The Fc portion of antibodies will bind to Fc receptors in two different ways. For example, after IgG and IgM bind to a pathogen by their Fab portion their Fc portions can bind to receptors on phagocytic cells (like macrophages) inducing phagocytosis.

The present knottin-Fc fusions can be implemented such that the Fc portion is used to provide dual binding capability, and/or for half-life extension, for improving expression levels, etc.

II. Knottin Fusions Used to Improve Ligand Receptor Binding

In this aspect of the present invention, a library of knottins having a randomized loop and fused to a receptor is screened and used as a platform to create improved ligand binding. As one example, an EETI library was fused to Axl, and this library was screened to isolate EETI-Axl binders with increased affinity to Gas6 ligand. Thus, knottins may be fused with an existing ligand (or receptor) as a general platform for increasing the affinity of a ligand-receptor interaction.

Here we show the potential for the engineering of proteins through the addition and subsequent optimization of a synthetic knottin binding domain. To demonstrate the power of this approach, we enhance a native high affinity (single-digit nanomolar) protein-protein interaction to subnanomolar levels using a single round of directed evolution. Through this work we also demonstrate that two structurally adjacent loops on the surface of the *Ecballium elaterium* trypsin inhibitor II (EETI-II) knottin can be simultaneously engineered to form a binding face towards an exogenous target. That is, a receptor and ligand may bind or be made to bind at an additional surface by engineering of a loop on a fused knottin, and/or engineering a loop in the receptor or ligand itself. This work demonstrates the potential for harnessing the natural evolutionary process of gene duplication and combination for laboratory evolution studies and should be broadly applicable to the study and optimization of protein function.

The domain addition and evolution strategy is a broad-based strategy for enhancing affinity of existing protein-protein interactions. A synthetic binding domain can be fused to the N- or C-terminus of a binding protein and subsequently evolved to enhance affinity to the binding partner by binding to an adjacent epitope. We also envision application in identification of binding proteins from "naïve" libraries. By "naïve" we mean libraries based off of proteins with no native binding affinity towards the target, e.g. the EETI-II knottin exhibits no native binding affinity towards Gas6. An additional application of this approach includes identification of binding proteins from naïve libraries. EETI-II peptides engineered for binding tumor targets hold significant promise for in vivo molecular imaging applications. However, identification of binding proteins from naïve libraries is challenging, in part due to the requirement that the affinity of the identified protein must be high enough for detection. For example, in yeast surface display binding affinities in the single-digit μM range are below the limits of detection and such proteins will generally not be enriched during library sorting. Domain addition and evolution can be used as an "anchoring" strategy, enabling identification of synthetic binding domains that enhance an existing interaction, but in isolation may themselves possess affinity below the limits of detection. In the example below, the EETI-II mutants developed here exhibit weak binding affinity towards Gas6 that are below the limits of detection when the knottin mutants are expressed in the absence of Axl. Subsequent affinity maturation through traditional strategies or further domain addition and evolution can be used to generate fully synthetic binding agents with high affinity.

III. Knottin Fusions to Enhance Expression of Folded, Functional Knottin Proteins Knottin peptides may be difficult to obtain in properly folded form. Chemical synthesis and refolding of peptides may be done, but requires extensive optimization. This problem can be mitigated by fusing the knottin to a protein. For example, EETI-II 2.5D (described below) could not be solubly expressed in yeast. However, when fused to Axl, a high yield of folded, functional knottin—Axl fusion was obtained. A protease cleavage site was introduced between EETI-II 2.5D and Axl to cut off the fusion partner. This is a general strategy where any fusion partner can be used for the expression, or it can be part of making a bispecific protein as described above.

This will also have implications for fusing modifying domains, such as Fc, human serum albumin, etc. to increase half-life for therapeutic applications.

By fusing a difficult to express knottin to a well-expressed protein, yields can be improved. A protease recognition sequence is inserted between the knottin and the fusion partner. This is exemplified below in Example 7.

Definitions

Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "effective amount" means an amount of a fusion protein of the present invention that is capable of modulating binding of an engineered peptide to a cognate binding partner. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

The term "knottin protein" means a structural family of small proteins, typically 25-40 amino acids, which hind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intra-chain disulfide bonds, which was found in several different microproteins with the same cysteine network, lent its name to this class of biomolecules. Although their secondary structure content is generally low, the knottins share a small triple-stranded antiparallel β-sheet, which is stabilized by the disulfide bond framework. Biochemically well-defined members of the knottin family, also called cysteine knot proteins, include the trypsin inhibitor EETI-IT from *Ecballium elaterium* seeds, the neuronal N-type Ca2+ channel blocker ω-conotoxin from the venom of the predatory cone snail Conus geographus, agouti-related protein (AgRP, See Millhauser et al., "Loops and Links: Structural Insights into the Remarkable Function of the Agouti-Related Protein." Ann. N.Y. Acad. Sci., Jun. 1, 2003; 994(1): 27-35), the omega agatoxin family, etc. A suitable agatoxin sequence is given in US 2009/0257952, having a common inventor with the present application. Another agatoxin sequence is given at GenBank® Accession number P37045. Omega-agatoxin-Aa4b; P81744, Omega-agatoxin-Aa3b, etc. Other knottin sequences may be found at GenBank® Accession number FJ601218.1, knottin [*Bemisia tabaci*]: Genbank Accession number P85079. Omega-lycotoxin: and Genbank Accession number AAB34917, mu-O conotoxin MrVIA=voltage-gated sodium channel blocker.

Conotxins generally consist of peptides which are 10-30 residues in length. A specific example is PRIALT® ziconotide, a synthetic equivalent of a naturally occurring conopeptide found in the piscivorous marine snail, Conus magus. Ziconotide, which is a 25 amino acid, polybasic peptide containing three disulfide bridges with a molecular weight of 2639 daltons and a molecular formula of $C_{102}H_{172}N_{36}O_{32}S_7$.

Knottin proteins have a characteristic disulfide linked structure. This structure is also illustrated in Gelly et al., "The KNOTTIN website and database: a new information system dedicated to the knottin scaffold," Nucleic Acids Research, 2004. Vol. 32, Database issue D156-D159. A triple-stranded β-sheet is present in many knottins. The cysteines involved in the knot are shown as connected by lines in FIG. 1D indicating which Cys residues are linked to each other. The spacing between Cys residues is important in the present invention, as is the molecular topology and conformation of the engineered loop. The engineered loop may contain RGD to provide an integrin binding loop. These attributes are critical for high affinity integrin binding. The RGD mimic loop is inserted between knottin Cys residues, but the length of the loop must be adjusted for optimal integrin binding depending on the three-dimensional spacing between those Cys residues. For example, if the flanking Cys residues are linked to each other, the optimal loop may be shorter than if the flanking Cys residues am linked to Cys residues separated in primary sequence. Otherwise, particular amino acid substitutions can be introduced that constrain a longer RGD-containing loop into an optimal conformation for high affinity integrin binding.

The present knottin proteins may contain certain modifications made to truncate the knottin, or to remove a loop or unnecessary cysteine residue or disulfide bond.

The term "amino acid" includes both naturally-occurring and synthetic amino acids and includes both the D and L form of the acids as well as the racemic form. More specifically, amino acids contain up to ten carbon atoms. They may contain an additional carboxyl group, and heteroatoms such as nitrogen and sulfur. Preferably the amino acids are α and β-amino acids. The term α-amino acid refers to amino acids in which the amino group is attached to the carbon directly attached to the carboxyl group, which is the α-carbon. The term β-amino acid refers to amino acids in which the amino group is attached to a carbon one removed from the carboxyl group, which is the β-carbon. The amino acids described here are referred to in standard IUPAC single letter nomenclature, with "X" meaning any amino acid.

The term "EETI" means Protein Data Bank Entry (PDB) 2ETI. Its entry in the Knottin database is EETI-II. It has the sequence (SEQ ID NO: 1)
GC PRILMRCKQDSDCLAGCVCGPNGFCG.

Full length EETI-II has a 30 amino acid sequence with a final proline at position 30:

(SEQ ID NO: 2)
1 GCPRILMR CKQDSDC LAGCVCGPNGFCGSP

Loops 1 and 3 are in bold and underlined. These loops can also be varied and affect binding efficiency, as is demonstrated below. Other loops may be varied without affecting binding efficiency.

The term "AgRP" means PDB entry 1 HYK. Its entry in the Knottin database is SwissProt AGRP_HUMAN, where the full-length sequence of 129 amino acids may be found. It comprises the sequence beginning at amino acid 87. An additional G is added to this construct. It also includes a C105A mutation described in Jackson, et al. 2002 Biochemistry, 41, 7565.

(SEQ ID NO: 3)
GCVRLHESCLGQQVPCCDPCATCYCRFFNAFCYCR-KLGTAMNPCSRT

The dashed portion shows a fragment omitted in the "mini" version, below. The bold and underlined portion, from loop 4, is replaced by the RGD sequences described below. Loops 1 and 3 are shown between brackets below:

(SEQ ID NO: 3)
GC[VRLHES]CLGQQVPCC[DPCAT]CYCRFFNAFCYCR-

KLGTAMNPCSRT

The term "mini" in reference to AgRP means PDB entry 1MRO. It is also SwissProt AGRP_HUMAN. It has the sequence, similar to that given above.

(SEQ ID NO: 4)
GCVRLHESCLGQQVPCCDPA̲ATCYCRFFNAFCYCR where the underlined "A" represents an amino acid substitution which eliminates a possible dimer forming cystine. (Cystine herein refers to the single amino acid; cysteine to the dimer.). The bold and underlined portion, from loop 4, is replaced by the below described RGD sequences.

The term "agatoxin" means omega agatoxin PDB 1OMB and the SwissProt entry in the knottin database TOG4B_AGFAP. It has the sequence (SEQ ID NO: 5)
EDN--CIAEDYGKCTWGGTKCCRGRPCRCSMIGTNCECT-

PRLIMEGLSFA

The dashes indicate portions of the peptide omitted for the "mini" agatoxin. An additional glycine is added to the N-terminus of the mini-construct. The bold and underlined portion is replaced by the below described RGD sequences.

The term "loop domain" refers to an amino acid subsequence within a peptide chain that has no ordered secondary structure, and resides generally on the surface of the peptide. The term "loop" is understood in the art as referring to secondary structures that are not ordered as in the form of an alpha helix, beta sheet, etc.

The term "substantial identity" in the context of a peptide indicates that a peptide comprises a sequence with at least 70% sequence identity to a reference sequence, preferably 80%, more preferably 85%, most preferably at least 90% or at least 95% sequence identity to the reference sequence over a specified comparison window, which in this case is either the entire peptide, a molecular scaffold portion, or a binding loop portion (~9-11 residues). Preferably, optimal alignment is conducted using the homology alignment algorithm of Needleman and Wunsch (1970) J. Mol. Biol., 48:443 453. An indication that two peptide sequences are substantially identical is that one peptide is immunologically reactive with antibodies raised against the second peptide. Another indication for present purposes, that a sequence is substantially identical to a specific sequence explicitly exemplified is that the sequence in question will have an integrin binding affinity at least as high as the reference sequence. Thus, a peptide is substantially identical to a second peptide, for example, where the two peptides differ only by a conservative substitution. "Conservative substitutions" are well known, and exemplified. e.g., by the PAM 250 scoring matrix. Peptides that are "substantially similar" share sequences as noted above except that residue positions that are not identical may differ by conservative amino acid changes. As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the NIH Multiple alignment workshop (http://helixweb.nih.gov/multi-align/). Three-dimensional tools may also be used for sequence comparison.

As used herein. "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "receptor tyrosine kinase" is used in its customary sense; examples are given below. The term "TAM receptor tyrosine kinase" refers to the TAM family of receptor kinases, including tyro3, Axl and MerTK. These am characterized by a conserved sequence within the kinase domain and adhesion molecule-like extracellular domains, and are described further in Linger et al. "TAM receptor tyrosine kinases: biologic functions, signaling, and potential therapeutic targeting in human cancer," Adv Cancer Res. 2008; 100:35-83.

General Description

Engineering of Knottin Peptides

An important feature of the present fusion proteins is that the knottin portion is used for specific binding to a predetermined ligand. The knottin binding is preferably engineered by replacing a native solvent exposed loop with a short (e.g. 5-12 amino acid) sequence that has been selected for binding to the predetermined ligand. The solvent-exposed (i.e. on the surface) loop will generally be anchored by disulfide-linked cysteine residues. The new, or replacement amino acid sequence is preferably obtained by randomizing codons in the loop portion, expressing the engineered peptide, and selecting the mutants with the highest binding to the predetermined ligand. This selection step may be repeated several times, taking the tightest binding proteins from the previous step and re-randomizing the loops.

The EETI-II knottin peptide contains a disulfide knotted topology and possesses multiple solvent-exposed loops that are amenable to mutagenesis. To evolve a binding interface with Gas6, we randomized the structurally adjacent loops 1 and 3. Fusion of this EETI-II loop library directly to the Axl Ig1 N-terminus (shown in FIG. 1D) did not perturb the native Gas6-Axl interaction, which thereby resulted in a background of tens of millions of single-digit nanomolar binders. The ability to isolate enhanced clones from such a background speaks to the power of yeast surface display and quantitative fluorescent-activated cell sorting for protein engineering. Moreover, a starting library that does not suffer from loss-of-function differs with that of traditional directed evolution strategies, where random mutation to one of the binding partners often results in decreased function for the majority of the initial library. Retention of wild-type properties in the domain addition naïve library sheds light on natural evolutionary landscapes, whereby domain addition and evolution in nature may allow for the evolution of protein function without the cost of decreased activity while exploring sequence space.

A wide variety of knottin peptides may be used in the present fusion proteins. For example, when displayed on the yeast cell surface, the following mutants bind to $\alpha_v\beta_3$ integrin about 2-3× better than a mutant with the RGD sequence from fibronectin.

TABLE 1

EETI sequences wherein the RGD motif (in italics in 1.4A) is found in the insert at positions 4-6.

| Peptide identifier | Sequence | SEQ ID NO: |
|---|---|---|
| 1.4A | GC*AEPRGDMPWTW*CKQDSDCLAGCVCGPNGFCG | (SEQ ID NO: 6) |
| 1.4B | GC*VGGRGDWSPKW*CKQDSDCPAGCVCGPNGFCG | (SEQ ID NO: 7) |
| 1.4C | GC*AELRGDRSYPE*CKQDSDCLAGCVCGPNGFCG | (SEQ ID NO: 8) |
| 1.4E | GC*RLPRGDVPRPH*CKQDSDCQAGCVCGPNGFCG | (SEQ ID NO: 9) |
| 1.4H | GC*YPLRGDNPYAA*CKQDSDCRAGCVCGPNGFCG | (SEQ ID NO: 10) |
| 1.5B | GC*TIGRGDWAPSE*CKQDSDCLAGCVCGPNGFCG | (SEQ ID NO: 11) |
| 1.5F | GC*HPPRGDNPPVT*CKQDSDCLAGCVCGPNGFCG | (SEQ ID NO: 12) |
| 2.3A | GC*PEPRGDNPPPS*CKQDSDCRAGCVCGPNGFCG | (SEQ ID NO: 13) |
| 2.3B | GC*LPPRGDNPPPS*CKQDSDCQAGCVCGPNGFCG | (SEQ ID NO: 14) |
| 2.3C | GC*HLGRGDWAPVG*CKQDSDCPAGCVCGPNGFCG | (SEQ ID NO: 15) |
| 2.3D | GC*NVGRGDWAPSE*CKQDSDCPAGCVCGPNGFCG | (SEQ ID NO: 16) |
| 2.3E | GC*FPGRGDWAPSS*CKQDSDCRAGCVCGPNGFCG | (SEQ ID NO: 17) |
| 2.3F | GC*PLPRGDNPPTE*CKQDSDCQAGCVCGPNGFCG | (SEQ ID NO: 18) |
| 2.3G | GC*SEARGDNPRLS*CKQDSDCRAGCVCGPNGFCG | (SEQ ID NO: 19) |
| 2.3H | GC*LLGRGDWAPEA*CKQDSDCRAGCVCGPNGFCG | (SEQ ID NO: 20) |
| 2.3I | GC*HVGRGDWAPLK*CKQDSDCQAGCVCGPNGFCG | (SEQ ID NO: 21) |
| 2.3J | GC*VRGRGDWAPPS*CKQDSDCPAGCVCGPNGFCG | (SEQ ID NO: 22) |
| 2.4A | GC*LGGRGDWAPPA*CKQDSDCRAGCVCGPNGFCG | (SEQ ID NO: 23) |
| 2.4C | GC*FVGRGDWAPLT*CKQDSDCQAGCVCGPNGFCG | (SEQ ID NO: 24) |
| 2.4D | GC*PVGRGDWSPAS*CKQDSDCRAGCVCGPNGFCG | (SEQ ID NO: 25) |
| 2.4E | GC*PRPRGDNPPLT*CKQDSDCLAGCVCGPNGFCG | (SEQ ID NO: 26) |
| 2.4F | GC*YQGRGDWSPSS*CKQDSDCPAGCVCGPNGFCG | (SEQ ID NO: 27) |
| 2.4G | GC*APGRGDWAPSE*CKQDSDCQAGCVCGPNGFCG | (SEQ ID NO: 28) |
| 2.4J | GC*VQGRGDWSPPS*CKQDSDCPAGCVCGPNGFCG | (SEQ ID NO: 29) |
| 2.5A | GC*HVGRGDWAPEE*CKQDSDCQAGCVCGPNGFCG | (SEQ ID NO: 30) |
| 2.5C | GC*DGGRGDWAPPA*CKQDSDCRAGCVCGPNGFCG | (SEQ ID NO: 31) |
| 2.5D | GC*PQGRGDWAPTS*CKQDSDCRAGCVCGPNGFCG | (SEQ ID NO: 32) |
| 2.5F | GC*PRPRGDNPPLT*CKQDSDCLAGCVCGPNGFCG | (SEQ ID NO: 33) |
| 2.5H | GC*PQGRGDWAPEW*CKQDSDCPAGCVCGPNGFCG | (SEQ ID NO: 34) |
| 2.5J | GC*PRGRGDWSPPA*CKQDSDCQAGCVCGPNGFCG | (SEQ ID NO: 35) |

The above engineered knottins contain the RGOD binding loop and bind specifically to integrins, as described in copending application Ser. No. 12/418,376, filed Apr. 3, 2009. As described there, these loops may be varied in the non-RGD residues to a certain degree without affecting binding specificity and potency. For example, if three of the eleven residues were varied, one would have about 70% identity to 2.5D. The above engineered knottins have been shown to bind specifically to $\alpha_v\beta_3$, $\alpha_v\beta_5$, and $\alpha_5\beta_1$ integrins Another example of a knottin peptide engineered to bind to integrins is AgRP. Table 2 below shows sequences of AgRP mutants isolated by flow cytometry and having an RGD sequence and flanking residues in loop 4, as indicated by the bolded residues:

TABLE 2

Sequences of additional AgRP mutants

| Clone | | Loop 4 sequence |
|---|---|---|
| 7A (5E) | (SEQ ID NO: 36) | GCVRLHESCLGQQVPCCDPAATCYCSGRGDNDLVCYCR |
| 7B | (SEQ ID NO: 37) | GCVRLHESCLGQQVPCCDPAATCYCKGRGDARLQCYCR |
| 7E | (SEQ ID NO: 38) | GCVRLHESCLGQQVPCCDPAATCYCVGRGDDNLKCYCR |
| 7J (6B) | (SEQ ID NO: 39) | GCVRLHESCLGQQVPCCDPAATCYCEGRGDRDMKCYCR |
| 7C | (SEQ ID NO: 76) | GCVRLHESCLGQQVPCCDPAATCYC YGRGDNDLRCYCR |

Additional AgRP engineered knottins can be made as described in the above-referenced US 2009/0257952 to Cochran et al. AgRP knottin fusions can be prepared using AgRP loops 1, 2 and 3, as well as loop 4 as exemplified above.

Engineered Knottin Binding Partners

The engineered knottin is fused to another protein. The protein will to some extent enter into the design of the engineered knottin according to the present description. That is, the fusion partner and the knottin binding partner will have a logical relationship in that they are in the same biological pathway, they are directed to targets which may be brought together to improve a therapeutic result, etc.

As exemplified below by an engineered knottin-tyrosine kinase receptor fusion, the fusion may be engineered to bind to a ligand for the tyrosine kinase. The fusion is administered and allowed to bind to the ligand, thereby acting as a decoy to prevent the native ligand from binding to the tyrosine kinase receptor. As further exemplified below, the entire tyrosine kinase receptor is not used; only portions that bind to a native ligand, preferably an agonist. In the case of Axl, the Ig1 and Ig2 portions of the Axl receptor that bind to the Gas6 ligand are used. Gas 6, growth arrest-specific 6) belongs to the family of plasma vitamin K-dependent proteins. Gas 6 shares high structural homology with an anticoagulant protein, but has growth factor-like properties through its interaction with receptor tyrosine kinases of the TAM family, tyro3, Axl and MerTK.

Another example of an engineered knottin-protein fusion is one where the fusion partner is a growth factor or active fragment of a growth factor, and the knottin is engineered to bind to endothelial cells such as may be present in the vasculature or on tumors. This is exemplified by a knottin (AgRP) engineered to bind $\alpha_v\beta_3$ integrins and a growth factor or growth factor fragment that binds to the Met receptor. Interaction between $\alpha_v\beta_3$ integrin and extracellular matrix is crucial for endothelial cells sprouting from capillaries and for angiogenesis. Furthermore, integrin-mediated outside-in signals co-operate with growth factor receptors to promote cell proliferation and motility. As another example, Soldi et al., "Role of alphav beta3 integrin in the activation of vascular endothelial growth factor receptor-2," The EMBO Journal (1999) 18, 882-892, reported that to determine a potential regulation of angiogenic inducer receptors by the integrin system, they investigated the interaction between $\alpha_v\beta_3$ integrin and tyrosine kinase vascular endothelial growth factor receptor-2 (VEGFR-2) in human endothelial cells. Both the VEGF receptor and the Met receptor (also known as hepatocyte growth factor receptor) are receptor tyrosine kinases.

Another example of binding partner selection is a fusion of an engineered knottin that binds to $\alpha_v\beta_3$ integrin and NK1, a fragment of the polypeptide growth factor HGF/SF which acts as agonist of the MET receptor. As described below, NK1 was modified to create highly stable, more effective agonistic ligands, or modified to create highly stable, more effective antagonists.

EETI-Axl Fusions with a Synthetic Binding Domain (Through Domain Addition)

In the examples below, the *Ecballium elaterium* trypsin inhibitor II (EETI-II) serves as a synthetic binding domain to increase binding of its fusion partner. EETI-II is a member of the knottin family of peptides which contain a characteristic interwoven disulfide-bonded framework that provides exquisite stability properties (FIG. 1B). The solvent exposed loops of EETI-II are tolerant to mutagenesis and have previously been individually engineered for novel recognition properties. However, in the present work, two structurally adjacent loops in EETI-II were concurrently randomized and the resulting library of EETI-II mutants was fused to wt Axl Ig1. Axl sequences are given in Entrez Gene Gene ID 558. This library was then screened to identify novel EETI-Axl fusions with enhanced Gas6 binding affinity. That is, binding would occur through the Axl receptor and through the engineered loops. We identified mutants with sub-nanomolar affinity following a single round of directed evolution, wherein both engineered loops of the EETI-II mutant contributed to the enhanced affinity towards Gas6 through the creation of a novel binding face. This work supports domain addition and evolution for enhancing protein function, and also supports the EETI-II knottin as a scaffold for engineering novel recognition properties.

Domain Addition Library Design and Synthesis

To enhance the affinity of the Gas6/Axl interaction we fused a loop library of the EETI-II knottin peptide to the Axl Ig1 since the Ig1 domain comprises the dominant binding site for Gas6. We chose a fusion to the Axl N-terminus because in the Gas6/Axl complex, the Axl Ig1 N-terminus is in closer proximity to Gas6 than its C-terminus, and is therefore more likely to enable interaction of the EETI-II mutants with Gas6 (FIG. 1C). Analysis of EETI-II and Axl structures shows fusion of EETI-II to the Axl N-terminus would give approximately 11 amino acid spacing between tertiary structures of the two proteins. Therefore, we chose to directly fuse the EETI-II loop library to the Axl N-terminus without inclusion of additional linker residues. The final Pro30 residue in EETI-II and Pro20 of Axl Ig1 were excluded to improve the flexibility of the linkage, resulting in EETI-II Ser29 fused directly to Axl Arg21. We chose EETI-II loops 1 and 3 for randomization as they are structurally adjacent (FIG. 1B), which would allow for the formation of a continuous binding face on the EETI-II knottin. Wild-type loops 1 and 3 were concurrently replaced with randomized sequences of 7-10 and 6-8 amino acids (FIG. 1D), respectively, using NNS codons. The NNS codon strategy permits the inclusion of all 20 amino acids in the engineered loops while limiting the frequency of stop codons by encoding for only one stop codon. Other degenerate library strategies could be employed. See, for other exemplary strategies, Kleeb et al., "Metabolic engineering of a genetic selection system with tunable stringency." Proc. Nat. Acad. Sci. 104: 13907-13912 (2007).

Direct fusion was achieved by inclusion of an AvrII (C'CTAG,G) site, which encodes for a proline-arginine dipeptide, prior to Axl Ig1 amino acid Gly22 in the yeast display pCT plasmid. The EETI-II loop library was designed to replace the first base pair of the restriction digested AvrII site with a 'T', to give TCTAGG (SEQ ID NO: 40), which encodes for the desired Ser-Arg linkage of EETI-II Ser29 and Axl Ig1 Arg21.

The cDNA for the EETI-II loop library was synthesized using standard PCR assembly techniques and the yeast display E-Axl library was generated by homologous recombination to the pCT-Avr-Axl acceptor plasmid (See Examples). This library is hereto referred to as the E-Axl library; it comprised $1.2 \times 10^8$ individual transformants as determined by dilution plating and colony counting. Sequence analysis of randomly selected individual clones confirmed intended fusion strategy, loop length distribution, and a lack of mutation to the Axl Ig1 sequence. Approximately 30% of the clones contained full loop sequences without stop codons or mutations in line with previous reports of libraries containing multiple randomized loops.

Identification of binding proteins from naïve libraries is challenging, in part due to the requirement that the affinity of the identified protein must be high enough for detection. For example, in yeast surface display binding affinities in the single-digit μM range are below the limits of detection and such proteins will generally not be enriched during library sorting. Domain addition and evolution can be used as an "anchoring" strategy, enabling identification of synthetic binding domains that enhance an existing interaction, but in isolation may themselves possess affinity below the limits of detection. In support of this, the EETI-II mutants developed here exhibit weak binding affinity towards Gas6 that are below the limits of detection when the knottin mutants are expressed in the absence of Axl. Subsequent affinity maturation through traditional strategies or further domain addition and evolution can be used to generate fully synthetic binding agents with high affinity.

Library Screening and Sequence Analysis

Expression of the E-Axl library and its binding to Gas6 were assessed by immunofluorescent labeling of the emyc epitope tag on the yeast display construct and the hexahistidine tag (SEQ ID NO: 77) on soluble Gas6, respectively (FIG. 2A). FIG. 2A shows the aga toxin component Aga 1p and Aga 2p extending in that order from the yeast cell wall, as is known in yeast surface display. An anti-his antibody tagged with Hylite 448 22 is bound to the his tag 32 on Gas 6; the myc tag 26 is bound to a chicken anti-myc antibody 28, which in turn is bound by an anti-chicken antibody labeled with Alexa 555, 30. A hemagglutinin tag is also included in the fusions. The Axl-Ig1 portion is fused to this, and binding of the Gas6 ligand to the Axl is carried out. Strikingly, all members of the starting library that expressed on the yeast cell surface bound to Gas6 at the same levels as wild-type Axl Ig1 FIG. 2B). This demonstrates that the direct fusion of an EETI-II loop library to the Axl N-terminus does not perturb the native Gas6-Axl interaction. Consequently, this also results in a background of tens of millions of wild-type, single-digit nanomolar binders from which rare improved clones must be separated.

Figure 3:
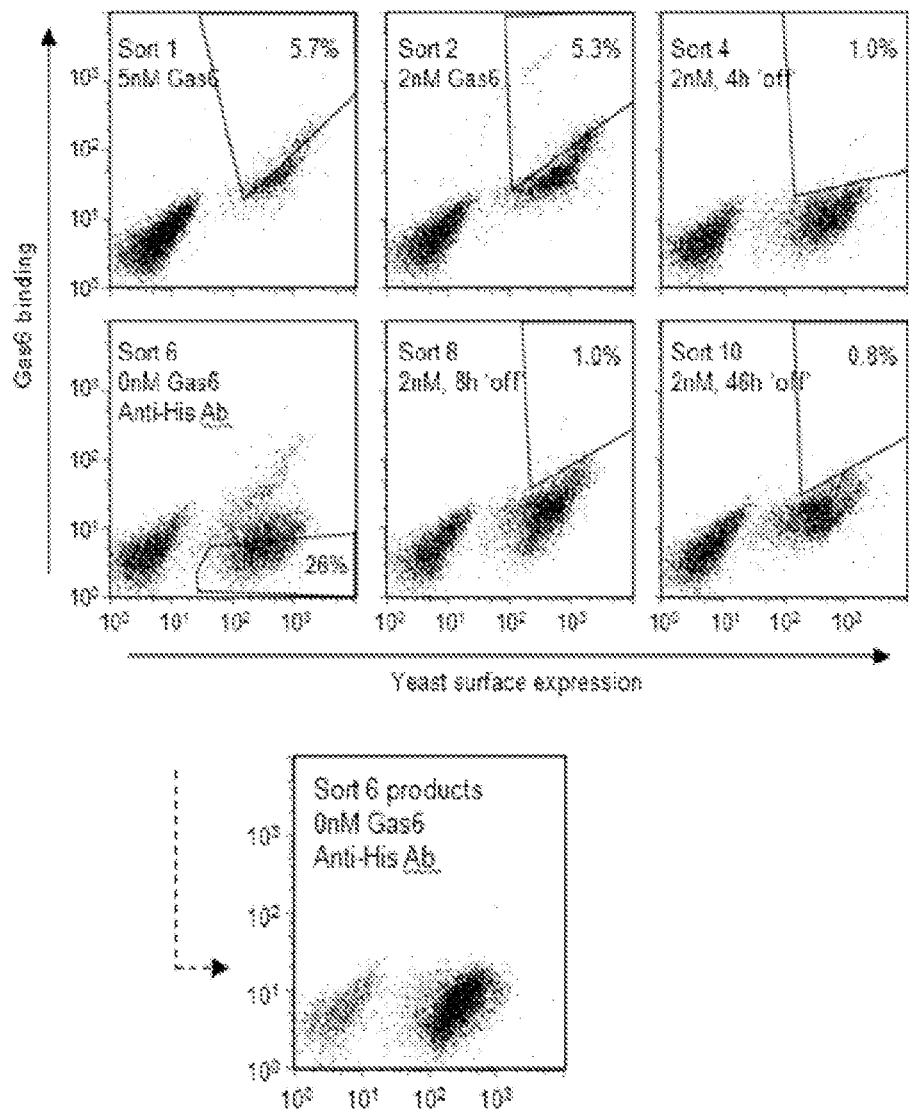
FIG. 3 is a set of scatter plots of results of EA-Axl library screening and sort progression.

For library screening using yeast surface display, often the top 1% of binding clones are collected; however, due to this extremely high background level of binding, we initially employed a conservative sort strategy wherein the top 6% of binding clones was collected to decrease probability of losing rare clones with enhanced properties (FIG. 3).

FIG. 3 shows that when sorting the library, the first sorts were conducted by screening for binding to soluble Gas6. Subsequent sorts used 'off-rate' sorts where binding to Gas6 was followed by incubation in the presence of excess competitor to impart selective pressure on enhanced kinetic dissociation. In the $6^{th}$ round of sorting we conducted a negative sort to clear mutants that were binding to secondary anti-His antibody. Sort 6 products (below) show these were completely eliminated with a single round of sorting. Final sort products retained binding after a 46 h unbinding ('off') step.

To increase stringency in later sort rounds, 'off-rate' sorts were conducted in which incubation with 2 nM Gas6 was followed by an unbinding step in the presence of a molar excess of soluble Axl receptor to serve as competitor. The excess competitor renders the dissociation of Gas6 from yeast-displayed E-Axl irreversible by sequestering free Gas6 in complex with soluble Axl receptor, thereby increasing the selective pressure for clones with slower dissociation rate.

Bispecific Proteins that Target Integrin and a Growth Factor Receptor

Described in Example 8 is the preparation of a fusion between a knottin (AgRP) engineered to bind $\alpha_v\beta_3$ integrins, and a fragment comprising the N-terminal and first kringle domains of HGF (termed NK1). This portion of HGF (hepatocyte growth factor) binds to the Met receptor. c-Met (MET or MNNG HOS Transforming gene) is a proto-oncogene that encodes a protein known as hepatocyte growth factor receptor (HGFR). The hepatocyte growth factor receptor protein possesses tyrosine-kinase activity. The primary single chain precursor protein is post-translationally cleaved to produce the alpha and beta subunits, which are disulfide linked to form the mature receptor.

The $\alpha_v\beta_3$ integrin receptor is over-expressed on many solid tumor cells making it an important cancer target. The Agouti related protein (AgRP), a cystine-knot peptide, contains four disulfide bonds and four solvent-exposed loops. It was engineered to target $\alpha_v\beta_3$ integrin receptors with pM binding affinity. The AgRP mutant, 7A, was shown to have the tightest binding affinity. The $K_D$ values of the 7A mutant against U87MG and K562-$\alpha_v\beta_3$ cells are 0.78 nM and 0.89 nM, respectively.

The Met receptor tyrosine kinase and its ligand hepatocyte growth factor (HGF) play an important role in mediating both tumor progression and tissue regeneration. The N-terminal and first kringle domains (NK1) of HGF is a naturally occurring splice variant that retains the ability to activate the Met receptor. However, NK1 is a weak agonist and is relatively unstable, limiting it therapeutic potential. We engineered NK1 mutants that function as Met receptor agonists and antagonists and possess enhanced biochemical and biophysical properties. As described below, we first evolved NK1 for enhanced stability and recombinant expression yield using yeast surface display. The NK1 mutants isolated from our library screens functioned as weak Met receptor antagonists, due to mutation of a residue which mediates NK1 homodimerization. We introduced point mutations that restored this NK1 homodimerization interface to create an agonistic ligand, or that further abolished these interactions to create more effective antagonists. The best antagonists exhibited melting temperatures up to ~64° C., a 15° C. improvement over antagonists derived from wild-type NK1, and up to a 40-fold improvement in expression yield.

The crosstalk between integrin and c-Met signaling pathways was studied and showed a significant relationship. The signal transduction of HGF/SF, the natural ligand of Met receptors, can induce ligand-binding activity in functionally-inactive $\alpha_v\beta_3$ integrins in epithelial and endothelial cells. Therefore, a dual-specific protein that targets and inhibits both $\alpha_v\beta_3$ integrin and Met receptors has promise as an effective cancer therapeutic, especially compared to single receptor targeting agents.

Receptor Tyrosine Kinase ("RTK") Fragments Useful in Fusions

The present fusion proteins may include a variety of receptor tyrosine kinases. These proteins have been well characterized as to their extracellular and ligand-binding motifs. They include RTK class I (EGF receptor family) (ErbB family); RTK class II (Insulin receptor family); RTK class III (PDGF receptor family); RTK class IV (FGF receptor family); RTK class V (VEGF receptors family); RTK class VI (HGF receptor family); RTK class VII (Trk receptor family); RTK class VIII (Eph receptor family); RTK class IX (AXL receptor family); RTK class X (LTK receptor family); RTK class XI (TIE receptor family); RTK class XII (ROR receptor family); RTK class XIII (DDR receptor family); RTK class XIV (RET receptor family): RTK class XV (KLG receptor family); RTK class XVI (RYK receptor family); and RTK class XVII (MuSK receptor family). Preferably, in preparing fusion proteins with these receptors, one would prepare a polypeptide containing only a portion of the receptor, i.e. containing the extracellular N-terminal region, which exhibits a variety of conserved elements including immunoglobulin (Ig)-like or epidermal growth factor (EGF-like domains, fibronectin type III repeats, or cysteine-rich regions that are characteristic for each subfamily of RTKs; these domains contain primarily a ligand-binding site, which binds extracellular ligands, e.g., a particular growth factor or hormone. The intracellular C-terminal region displays the highest level of conservation and comprises catalytic domains responsible for the kinase activity of these receptors, which catalyses receptor autophosphorylation and tyrosine phosphorylation of RTK substrates.

Receptor tyrosine kinase sequences are available from a variety of sources, including Genbank. Exemplary sequences that may be used to create fragments and fusion proteins according to the present invention are given. e.g. in Rand et al., "Sequence survey of receptor tyrosine kinases reveals mutations in glioblastomas." Proc. Nat. Acad. Sci. Oct. 4, 2005 vol. 102 no. 40 14344-14349. The following list is taken from that publication.

| Genbank Accession Number | RTK Description |
|---|---|
| NM_004439 | Ephrin type-A receptor 5 precursor |
| NM_001982 | Receptor tyrosine-protein kinase erbB-3 precursor |
| NM_020975 | Proto-oncogene tyrosine-protein kinase receptor ret precursor |
| NM_002944 | Proto-oncogene tyrosine-protein kinase ROS precursor |

-continued

| Genbank Accession Number | RTK Description |
|---|---|
| NM_002530 | NT-3 growth factor receptor precursor |
| NM_002019 | Vascular endothelial growth factor receptor 1 precursor |
| NM_005012 | Tyrosine-protein kinase transmembrane receptor ROR1 precursor |
| NM_004560 | Tyrosine-protein kinase transmembrane receptor ROR2 precursor |
| NM_004304 | ALK tyrosine kinase receptor precursor |
| NM_000222 | Mast/stem cell growth factor receptor precursor |
| NM_006180 | BDNF/NT-3 growth factors receptor precursor |
| NM_006206 | Alpha platelet-derived growth factor receptor precursor |
| NM_004441 | Ephrin type-B receptor 1 precursor |
| NM_000875 | Insulin-like growth factor I receptor precursor |
| NM_004438 | Ephrin type-A receptor 4 precursor |
| NM_000208 | Insulin receptor precursor |
| NM_004119 | FL cytokine receptor precursor |
| NM_006182 | Discoidin domain receptor 2 precursor |
| NM_000141 | Fibroblast growth factor receptor 2 precursor |
| NM_023110 | Basic fibroblast growth factor receptor 1 precursor. |

See also, Lee et al., "Vascular endothelial growth factor-related protein: a ligand and specific activator of the tyrosine kinase receptor Flt4." PNAS Mar. 5, 1996 vol. 93 no. 5 1988-1992.

The exact fragment of the receptor to be used in the present invention can be determined in view of the present teachings and existing knowledge of receptor structure. It is not necessary that an exact sequence that encodes only the ligand binding pocket be used. Some flexibility to include additional amino acids is tolerated. For example, as disclosed in US 20040132634. The N-terminal extracellular region of all Eph family members contains a domain necessary for ligand binding and specificity, followed by a cysteine-rich domain and two fibronectin type II repeats. In general, the N terminal portion, of about 400, 500 or 600 amino acids may be used as a ligand binding fragment of a receptor tyrosine kinase.

The above listings provide amino acid and nucleotide sequences. Other nucleotide sequences may be obtained from Genbank by searching on the name of the peptide or protein. Knottin DNA sequences may be obtained from the given amino acid sequences, using any codon assignment; codon assignment may be selected based on the expression vector used, such as yeast. An EETI nucleotide sequence is given in WO0234906, GenBank AX497055; an AGRP nucleotide sequence may be found at NG_011501; an agatoxin nucleotide sequence may be found at Genbank M95540.1. Another knottin amino acid and nucleic acid sequence may be found in J. Microbiol. Biotechnol. (2010), 20(4), 708-711, relating to the knottin Psacotheasin.

Receptor Ligand Fragments Useful in Fusions

Exemplified here are the particular receptor ligands hepatocyte growth factor and the antibody Fc fragment. The hepatocyte growth factor (also termed c-met) was fragmented to yield the portion of it that is known to bind to the met receptor. This fragment of HGF is known as the NK1 fragment. An exemplary sequence is given in SEQ ID NO: 66. This sequence contains portions of sequences in the PAN_Apple super family and of the KR superfamily. Therefore, one would expect that the presently exemplified compositions, given the present teachings, could be expanded to include hepatocyte growth factor-like proteins; plasminogen domain containing proteins; macrophage stimulating factor 1; and other plasminogen-related growth factors such as RON ("recepteur d'origine Nantais"). See. Maestrini et al., "A family of transmembrane proteins with homology to the MET-hepatocyte growth factor receptor," PNAS Jan. 23, 1996 vol. 93 no. 2 674-678. Also, in mammals, hepatocyte growth factor is a homolog of serine proteases but it has lost its proteolytic activity.

Administration of Bispecific Proteins

The present fusion proteins may be administered in vitro, such as in cell culture studies, or to cells intended for transplant, but may also be administered in vivo. A variety of formulations and dosing regiments used for therapeutic proteins may be employed. The pharmaceutical compositions may contain, in addition to the CFP, suitable pharmaceutically acceptable carriers, biologically compatible vehicles and additives which are suitable for administration to an animal (for example, physiological saline) and eventually comprising auxiliaries (like excipients, stabilizers or diluents) which facilitate the processing of the active fusion proteins into preparations which can be used pharmaceutically. Such compositions can be eventually combined with another therapeutic composition acting synergically or in a coordinated manner with the chimeric proteins of the invention. Alternatively, the other composition can be based with a fusion protein known to be therapeutically active against the specific disease (e.g. herceptin for breast cancer). Alternatively, the pharmaceutical compositions comprising the soluble can be combined into a "cocktail" for use in the various treatment regimens.

The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

Any accepted mode of administration can be used and determined by those skilled in the art to establish the desired blood levels of then fusion protein. For example, administration may be by various parenteral routes such as subcutaneous, intravenous, epidural, topical, intradermal, intrathecal, direct intraventricular, intraperitoneal, transdermal (e.g. in slow release formulations), intramuscular, intrapcritoncal, intranasal, intrapulmonary (inhaled), intraocular, oral, or buccal routes.

Other particularly preferred routes of administration are aerosol and depot formulation. Sustained release formulations, particularly depot, of the invented medicaments are expressly contemplated.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active fusion proteins as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active fusion protein together with the excipient. Compositions that can be administered rectally include suppositories.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain is otonicity (e.g. mannitol) or chemical stability (e.g. preservatives and buffers). The formulation is sterilized by commonly used techniques. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active fusion proteins may be dissolved or suspended in suitable liquids, such as fatty oils, liquid paraffin, or liquid polyethylene glycols. In addition, stabilizers may be added. All formulations for oral administration should be in dosages suitable for such administration.

The fusion proteins may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents. Alternatively, the active ingredient may be in powder or lyophilized form for constitution with a suitable vehicle, such as sterile pyrogen-free water, before use.

In addition to the formulations described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt. Additionally, the fusion proteins may be delivered using a sustained release system, such as semipermeable matrices of solid hydrophobic polymers containing the therapeutic agent. Various sustained-release materials have been established and are well known by those skilled in the art. Sustained release capsules may, depending on their chemical nature, release the fusion proteins for a few weeks up to over 100 days or one year.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active protein is comprised between 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual. According to the invention, the substances of the invention can be administered prophylactically or therapeutically to an individual prior to, simultaneously or sequentially with other therapeutic regimens or agents (e.g. multiple drug regimens), in a therapeutically effective amount. Active agents that are administered simultaneously with other therapeutic agents can be administered in the same or different compositions.

For any protein used in the method of the invention, the therapeutically effective dose can be estimated initially from cell culture assays. For example, a dose can be formulated in animal models to achieve a circulating concentration range that includes or encompasses a concentration point or range shown to decrease cytokine expression in an in vitro system. Such information can be used to more accurately determine useful doses in humans. A therapeutically effective dose refers to that amount of the fusion protein that results in amelioration of symptoms in a patient. Toxicity and therapeutic efficacy of such fusion proteins can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Fusion proteins that exhibit high therapeutic indices are preferred. The data obtained from these cell culture assays and animal studies can be used in formulating a range of dosage for use in humans. The dosage of such fusion proteins lies preferably within a range of circulating concentrations that include the ED50. with little or no toxicity. The dosage may vary within this range depending upon the dosage form employed and the route of administration utilized. The exact formulation, route of administration and dosage can be chosen by the individual physician in view of the patient's condition.

EXAMPLES

As described in Examples 1 through 5, we have developed a general approach to engineering existing protein-protein interactions we refer to as "domain addition and evolution" in which enhancement is accomplished by expanding the binding interface through the addition and subsequent in vitro evolution of a synthetic binding domain. We validate this approach by showing the ability to enhance the native high affinity ligand-receptor interaction between Gas6 and the Axl receptor through addition and evolution of a synthetic knottin binding domain.

We identified EETI-II-axl fusion mutants with up to 4-fold enhanced affinity towards Gas6. Importantly, Axl Ig1 did not accumulate mutations during the mutagenesis and screening process, indicating that the enhancement in affinity can be attributed to the engineered EETI-II mutants. Individual reversion of the engineered loops to wild-type EETI-II sequence confirmed some EA mutants require both engineered loops for the enhanced affinity. To our knowledge, this is the first instance of engineering two loops of a knottin into a binding face towards an exogenous target. Also, the three EA mutants each comprise approximately 45% non-native EETI-II amino acid sequence. Together, this further validates the robust nature of the knottin fold for generating novel binding reagents. This work is also relevant given the role of Axl in cancer metastasis. Dominant negative Axl receptors suppress tumor cell migration and metastasis (Vajkoczy et al., 2006; Rankin et al., 2010), and the enhanced affinity EA mutants may be useful therapeutic candidates.

An additional application of this approach includes identification of binding proteins from naïve libraries. EETI-II peptides engineered for binding tumor targets hold significant promise for in vivo molecular imaging applications. However, identification of binding proteins from naïve libraries is challenging, in part due to the requirement that the affinity of the identified protein must be high enough for detection. For example, in yeast surface display binding affinities in the single-digit μM range are below the limits of detection and such proteins will generally not be enriched during library sorting. Domain addition and evolution can be used as an "anchoring" strategy, enabling identification of synthetic binding domains that enhance an existing interaction, but in isolation may themselves possess affinity below the limits of detection. In support of this, the EETI-II mutants developed here exhibit weak binding affinity towards Gas6 that are below the limits of detection when the knottin mutants are expressed in the absence of Axl. Subsequent affinity maturation through traditional strategies or further domain addition and evolution can be used to generate fully synthetic binding agents with high affinity.

As described below, the engineered EETI knottin variant 2.5D, which binds to $\alpha v\beta 3/\alpha v\beta 5$ integrin was directly fused to the N-terminus of wt Axl Ig1. The concept of this multi-specific fusion protein was validated using yeast-surface display by showing that EETI 2.5D—Axl bound to $\alpha v\beta 3$ integrin and Gas6 at levels comparable to the mono-specific proteins EETI2.5D and Axl, respectively. Furthermore, binding of $\alpha v\beta 3$ integrin or Gas6 was not affected by the presence of a saturating concentration of the other target, suggesting EETI 2.5D—Axl is capable of simultaneously interacting with both $\alpha v\beta 3$ integrin and Gas6. The EETI 2.5D—Axl fusion protein was able to be produced recombinantly in microbial hosts on a scale of 35 mg/L. The resulting protein displayed high affinity ($K_D$~2 nM) to $\alpha v\beta 3$ integrin expressed on the cell surface.

Example 1: Reagents and Media

SD-CAA media contained 20 g/L glucose, 6.7 g/L yeast nitrogen base without amino acids, 5.4 g/L Na2HPO4, 8.6 g/L NaH2PO4.H2O, and 5 g/L Bacto casamino acids; SG-CAA media was identical, except glucose was substituted with 20 g/L galactose. SD-CAA pH 4.5 media was identical to SD-CAA, except phosphates were replaced with 13.7 g/L sodium citrate dihydrate, 8.4 g/L citric acid anhydrous, and adjusted to pH 4.5. Gas6 and Axl-Fc proteins were purchased from R&D Systems, chicken anti-cmyc and goat anti-chicken Alexa 555 antibodies were purchased from Invitrogen, mouse anti-His Hilyte Fluor 488 monoclonal antibody was purchased from Anaspec. Phosphate buffered saline (PBS) is composed of 11.9 mM sodium phosphate pH 7.4, 137 mM sodium chloride, 2.7 mM potassium chloride. PBS/BSA consisted of PBS with 1 mg/mL bovine serum albumin.

Example 2: Yeast Surface Display Library Generation: EETI/Axl Fusions

Four forward assembly primers replacing EETI-II loop 1 with 7, 8, 9 or 10 degenerate NNS codons and three reverse assembly primers replacing EETI-II loop 3 with 6, 7 or 8 degenerate NNS codons was used to assemble the EETI-II loop library. (EETI-II amino acid sequence is Genbank Accession No. P12071; DBNA sequences are given in copending U.S. Ser. No. 12/418,376, filed Apr. 3, 2009, also incorporated by reference. DNA sequences may designed as desired by reverse translation of the amino acid sequences given.) The primer sequences were complementary to the regions adjacent the loops. The amino acid sequences of EETI-II and the randomized loop 1 and loop 3, as well as the loops randomized in Axl are shown in FIG. 1D. The four forward primers were pooled and used at 1 µM each, and each of the three reverse primers were pooled and used at 1.33 µM each, with 1× KOD polymerase buffer, 0.2 mM dNTPs, 1.5 mM MgCl$_2$, 1 M Betaine, and 2.5 units KOD polymerase (Novagen). Thermocyling parameters were: Step 1-95° C. for 2 min; Step 2-95° C. for 30 sec, 55° C. for 30 sec, 72° C. for 1 min (30 cycles): Step 3-72° C. for 10 min. Assembled DNA (0.6 µL) was amplified using 2 µM forward and reverse amplification primers, 1× Pfx50 buffer, 0.2 mM dNTPs, and 5 units Pfx50 DNA polymerase (Invitrogen). Forward amplification primer had 50 bp homology to the pCT backbone, while the reverse amplification primer contained 50 bp homology to the Axl Ig1 N-terminus and was designed to ensure appropriate Ser-Arg linkage of the EETI-II C-terminus (Ser29) with the Axt Ig1 N-terminus (Arg21). For preparation of the plasmid backbone, Axl amino acids comprising the Ig1 domain (22-132; Genbank Accession NO. P30530) were cloned into the yeast display pCT plasmid (Boder and Wittrup, 1997) using NheI and BamHI restriction sites. We included an AvrII restriction site directly 5' of the Axl sequence. This was placed downstream of the NheI site with a 14 bp spacer of "junk DNA" to facilitate restriction digest. We termed this plasmid pCT Avr-Axl. Plasmid backbone for library synthesis was generated by digesting pCT Avr-Axl with NheI and AvrII restriction enzymes. A total of ~50 µg of cDNA insert and ~25 µg of restriction digested pCT Avr-Axl backbone was transformed into EBY100 by electroporation and assembled in vivo by homologous recombination. A library of 1.2×10$^8$ transformants was obtained, as estimated by serial dilution plating and colony counting. Sequence analysis of randomly selected clones confirmed appropriate fusion of EETI-II with Axl Ig1 and desired loop length distribution in the EETI-II mutants.

Yeast surface display is described further in U.S. Pat. No. 6,423,538. Generally, at least 10$^4$ transformants will be obtained.

Primers were designed as follows:
DNA Oligonucleotide Primers for EETI-Axl Library Synthesis/Assembly and Amplification In the sequences below, the nucleotides used for homology to the plasmid backbone are shown at the 5' end up to the first slash. The part of the primer between the first slash and the double slash and the triple slash and the 3' end correspond to residues of EETI-II. N stands for any nucleotide and S is a mixture of G and C. The pal of the primer between the double slash and the triple slash are nucleotides used to produce randomized residues for EETI-II loop 1 or loop 3.

L1_7X_fwd:
(SEQ ID NO: 67)
Ggttctgctagc/ggttgt//nnsnnsnnsnnsnnsnnsnns/// tgtaaacaagattctgattgtttggctggttgtgtt

L1_8X_fwd:
(SEQ ID NO: 68)
Ggttctgctagc/ggttgt//nnsnnsnnsnnsnnsnnsnnsnns/// tgtaaacaagattctgattgtttggctggttgtgtt

L1_9X_fwd:
(SEQ ID NO: 69)
Ggttctgctagc/ggttgt//nnsnnsnnsnnsnnsnnsnnsnnsnns/// tgtaaacaagattctgattgtttggctggttgtgtt

L1_10X_fwd:
(SEQ ID NO: 70)
Ggttctgctagc/ggttgt// nnsnnsnnsnnsnnsnnsnnsnnsnns/// tgtaaacaagattctgattgtttggctggttgtgtt

In the case of the reverse primers below, the 5' end up to the first slash was homologous to nucleotides encoding the N terminus of the Axl receptor construct, which is also part of the acceptor plasmid backbone. As above, the region between the first slash and the double slash and the triple slash and the 3' end correspond to residues of EETI-II. N stands for any nucleotide and S is a mixture of G and C.

L3_6X_rev:
(SEQ ID NO: 71)
Cgtgcccct/gagaccaca//snnsnnsnnsnnsnnsnn/// acaaacacaaccagccaaacaatcag

L3_7X_rev:
(SEQ ID NO: 72)
Cgtgcccct/gagaccaca//snnsnnsnnsnnsnnsnnsnn/// acaaacacaaccagccaaacaatcag

L3_8X_rev:
(SEQ ID NO: 73)
Cgtgcccct/gagaccaca//snnsnnsnnsnnsnnsnnsnn/// acaaacacaaccagccaaacaatcag

After library synthesis by PCR assembly, the library was amplified using the amplification primers below, which contain ~50 base pairs of homology to the plasmid backbone (underlined, which comprises homology to the Axl sequence for the case of the reverse amplification primer). The ~50 base pairs of homology allows for assembly of the library insert and plasmid backbone as described by "Raymond CK, Pownder TA, Sexson SL, 1999. General method for plasmid construction using homologous recombination. Biotechniques 26:134-138, 140-131."

Library_amplification_reverse:
(SEQ ID NO: 74)
Ttccctgggttgcccacgaagggactttcttcagcctgcgtgcccct/ gctaccaca

Library_amplification_forward: (homology to plasmid backbone portion is 5' of slash)
(SEQ ID NO: 75)
Ggtggttctggtggtggtggttctggtggtggtggttctgctagc/ ggttgt

Example 3: Library Screening with Gas6

Various concentrations of Gas6 were incubated with yeast-displayed libraries in PBS/BSA for ~2-3 hr at room temperature. For the final hour, chicken anti-cmyc antibodies were added to a final dilution of 1:250. Cells were pelleted by centrifugation, washed with 1 mL ice cold PBS/BSA, and resuspended in PBS/BSA containing 1:100 dilution of goat anti-chicken A555 and 1:100 dilution of mouse anti-His 488 antibodies for 25 min on ice. Cells were pelleted, washed with 1 mL ice cold PBS/BSA, and sorted by fluorescence-activated cell sorting (FACS) on a Vantage SE flow cytometer (Stanford FACS Core Facility). Collected cells were amplified in SD-CAA pH 4.5 media and induced for expression in SG-CAA media at 30° C. for additional rounds of FACS to yield an enriched pool of mutants. The first round of sorting by FACS consisted of three separate sorts for a total of approximately 8×10$^7$ sorted cells, while subsequent sort rounds analyzed at least 10× the number of yeast collected in the previous round to ensure sufficient sampling of remaining library diversity. Sort stringency was increased by decreasing the concentration of Gas6. In the later sort rounds, following incubation with Gas6 cells were pelleted, washed, and incubated in the presence of excess competitor (~50-fold molar excess of Axl-Fc) for "off-rate" sorts. In the final hour of the unbinding step chicken anti-cmyc was added to 1:250 final dilution. Cells were pelleted, washed, and stained with secondary antibodies as above. Plasmid DNA was recovered from yeast cultures using a Zymoprep kit (Zymo Research) and transformed into XL-1 blue supercompetent *E. coli* cells (Stratagene) for plasmid miniprep. DNA sequencing was performed by MC Lab (South San Francisco, Calif.).

After five rounds of sorting, the library began to enrich for clones possessing stronger binding than wild-type Axl Ig1 (FIG. 3). A common problem in screening libraries containing randomized sequences is the potential to screen for artifactual binders. For example, since we are illuminating Gas6 binding using an anti-hexahistidine secondary antibody ("hexahistidine" disclosed as SEQ ID NO: 77), some of the "enhanced" clones actually bound to the secondary antibody. To control for this, we conducted a negative sort with 0 nM Gas6 and secondary antibody labeling as usual to clear secondary binders from the collected pool (FIG. 3, Sort 6). We continued to monitor for secondary binders, but this single negative sort was sufficient for eliminating artifactual binders from all subsequent sort products. Ultimately, we obtained an enriched pool of mutants with enhanced binding to Gas6 over wild-type Axl Ig1. For comparison, the final sort, which used a 46 h 'off' step, exhibited higher persistent binding than the fourth sort, which only used a 4 h 'off' step, demonstrating significant improvement in kinetic dissociation rate.

Example 4: Characterization of Engineered Mutants

Gas6 (0.05-400 nM) was added to 5×10$^4$ yeast cells displaying protein of interest in PBS/BSA at room temperature, using volumes, cell numbers, and incubation times experimentally determined to avoid ligand depletion and reach binding equilibrium. Cells were pelleted and washed with ice cold PBS/BSA and resuspended in PBS/BSA containing 1:250 dilution of chicken anti-cmyc and incubated on ice for 40 min. Cells were pelleted, washed and resuspended in PBS/BSA containing a 1:100 dilution of goat anti-chicken and mouse anti-His secondary antibodies for 20 min on ice. Cells were washed and analyzed using a FACSCalibur flow cytometer (Becton Dickinson) and FlowJo software (Treestar, Inc). Binding titrations were fit to a four-parameter sigmoidal curve using Kaleidagraph software to determine the equilibrium binding constant ($K_D$). For kinetic unbinding tests cells were incubated with 2 nM Gas6 until binding equilibrium was reached, then were washed, pelleted, and incubated in the presence of 50-fold molar excess Axl-Fc as described above for off-rate sorts for 0, 1, 4, 9.25, 23, or 46 hrs. Persistent binding was analyzed by flow cytometry and unbinding was fit to a single or double exponential decay curves as appropriate using Kaleidograph software. Persistent binding for reversion to wild-type EA loop variants was conducted identically to the kinetic binding tests, except unbinding step was conducted for 0-9.25 hrs.

Sequencing a total of 31 randomly selected clones from products of the 7$^{th}$, 8$^{th}$, and 9$^{th}$ rounds of sorting revealed twelve unique clones, with a 10$^{th}$ round of sorting enriching for two of the clones from the 9$^{th}$ round sort products (Table 3, below). All clones exhibited loop lengths in line with the initial library design and no clones contained mutations in the Axl sequence, indicating the enhanced affinity of EA clones is specific to the EETI-II mutants. Three of the twelve clones contained a PGM motif in loop 3, with two additional clones containing either PTM or PGK, for a common P-G/T-M/K motif. There was also lesser occurrence an L or L-X preceding and R-S succeeding the P-G/T-M/K motif (FIG. 1D). Interestingly, only four of the twelve EA mutants, EA 7.01, EA 7.05, EA7.06, and EA 8.04, did not contain cysteines in the engineered loops, but one of these, EA 7.05, contained a cys to arg mutation in the conserved cysteine residue preceding loop 1. Some mutants containing the P-T/G-M/K motif in loop 3 also contained a cysteine in an engineered loop, suggesting the additional cysteines may not completely perturb the EETI-II loop structure (Table 3). However, to minimize potential effects of unpaired cysteines, EA 7.01, 7.06, and 8.04 were selected for further investigation. For brevity, the entire sequences of the Axl fusions is not given here, although are set forth in the attached sequence listing for SEQ ID NOs: 41, 46 and 50. It is understood that the Axl Ig1 sequence is set forth below in both native and mutated forms and is used in the EA sequences below in native form, except where noted. For example, EA 7.01 as listed in Table 3 is fused to the N terminal of Axl Ig1 continues with the N terminal sequence of the Axl Ig1 sequence, as shown in FIG. 1D and in SEQ ID NO: 41. The other EAs listed in table 3 are similarly fused with the Axl sequence beginning "RGT . . . " . . . Full length sequences are given in SEQ ID NOs: 41, 46 and 50, illustrated in FIG. 1D up to the 'QAE . . . " portion. To reiterate, in the polypeptides of Table 3 below, the terminal GS is fused to the Axl Ig1 domain as shown in SEQ ID NO: 84, below.

TABLE 3

Sequences of EA products from final sort rounds

| Clone* | AA sequence | #AA L1** | #AA L3** | #rpt | SEQ ID NO: | Notes |
|---|---|---|---|---|---|---|
| Wt EETI-II | GC PRILMR CKQDSDCLAGCVC GPNGF CGSP | 6 | 5 | | 2 | |
| EA 7.01 | GC ALMTPSAVD CKQDSDCLAGCVC LPGMVR CGS | 9 | 6 | 2 | Residues 1-33 of SEQ ID NO: 41 | |

TABLE 3-continued

Sequences of EA products from final sort rounds

| Clone* | AA sequence | #AA L1** | #AA L3** | #rpt | SEQ ID NO: | Notes |
|---|---|---|---|---|---|---|
| EA 7.02 | GC LGNVRACVSV CKQDSDCLAGCVC ELARSNK CCGS | 6, 10 | 7, 8 | 1 | 42 | |
| EA 7.03 | GC TAVRPCT CKQDSDCLAGCVC TLLPGMLM CGS | 5, 7 | 8 | 1 | 43 | |
| EA 7.04 | GC WPRVSCVLWH CKQDSDCLAGCVC ILTRHKTV CGS | 5, 10 | 8 | 1 | 44 | |
| EA 7.05 | GR RWWTLAR CKQDSDCLAGCVC ILDPGKRS CGS | '7' | 8 | 1 | 45 | |
| EA 7.06 | GC LGGVALAH CKQDSDCLAGCVC HILPEL CGS | 8 | 6 | 1 | | Residues 1-32 of SEQ ID NO: 46 |
| EA 7.08 | GC HENGLPLI CKQDSDCLAGCVC SSHNWCQ CGS | 8 | 5, 7 | 1 | 47 | |
| EA 8.01 | GC ALMTPSAVD CKQDSDCLAGCVC LPGMVR CGS | 9 | 6 | 6 | 48 | Same as 7.01 |
| EA 8.02 | GC VCLCCGPSGS CKQDSDCLAGCVC AANHKDN CGS | ??, 10 | 7 | 3 | 49 | |
| EA 8.04 | GC SWSTLAR CKQDSDCLAGCVC MLEPGMRS CGS | 7 | 8 | 2 | | Residues 1-33 of SEQ ID NO: 50 |
| EA 8.05 | GC WLECWYR CKQDSDCLAGCVC YLCPTMGS CGS | 3, 7 | 5, 8 | 3 | 51 | |
| EA 8.08 | GC LGNVRACVSV CKQDSDCLAGCVC ELARSNK CCGS | 6, 10 | 7, 8 | 1 | 52 | Same as 7.02 |
| EA 9.01+ | GC VRVASHLWF CKQDSDCLAGCVC CGRPNV CGS | 9 | 5, 6 | 3 | 53 | |
| EA 9.02 | GC VCLCCGPSGS CKQDSDCLAGCVC AANHKDN CGS | ??, 10 | 7 | 2 | 54 | Same as 8.02 |
| EA 9.05 | GC CSLRWCVSRV CKQDSDCLAGCVC INPNKPL CGS | ??, 10 | 7 | 2 | 55 | |
| EA 9.07 | GC ALMTPSAVD CKQDSDCLAGCVC LPGMVR CGS | 9 | 6 | 1 | 56 | Same as 7.01 |
| EA 10.01* | GC VRVASHLWF CKQDSDCLAGCVC CGRPNV CGS | 9 | 5, 6 | 2 | 57 | Same as 9.01 |
| EA 10.02 | GC CSLRWCVSRV CKQDSDCLAGCVC INPNKPL CGS | ??, 10 | 7 | 6 | 58 | Same as 9.05 |

*Randomly selected clones from products of 7th, 8th, 9th or 10th round of sorting. All clones retained wild-type Axl Ig1 sequence (not shown).
**If cysteines are present in loop, then total loop length and "shortened" loop length are noted.
+Contains in-frame G3S (SEQ ID NO: 78) insertion in (G4S)3 linker (SEQ ID NO: 79).
rpt: number of times that clone occurred in the randomly selected clones for sequencing.

Example 5: Characterization of Axl Variants to Gas6

In order to use yeast display to characterize the binding interactions between Gas6 and the engineered EA mutants, we first sought to confirm that yeast display allows to accurate affinity measurements of the Gas6-Axl interaction. Using yeast displayed Axl we were able to recapitulate previously reported binding affinities of Axl variants determined by surface plasmon resonance and solid phase binding (Table 4). This validates that yeast-displayed Axl is similar to recombinant versions of the receptor.

TABLE 4

Comparison of affinity of Axl point mutants by yeast surface display (YSD) to values reported in the literature.

|  | $K_D$ (nM) YSD* | Solid phase [+] | SPR [+] |
|---|---|---|---|
| Wt Axl | 1.7 ± 0.6 | 1 | 6 ± 2 |
| E56R | 10.2 ± 3.6 | 6 | 10 ± 2 |
| E59R | 109.2 ± 17.6 | 40 | 98 ± 24 |
| T77R | >200 | >200 | 311 ± 118 |

*This work
[+] From ref (Sasaki et al., 2006 Structural basis for Gas6-Axl signalling, EMBO J. 2006 Jan. 11; 25(1): 80-87.)

Figure 4:
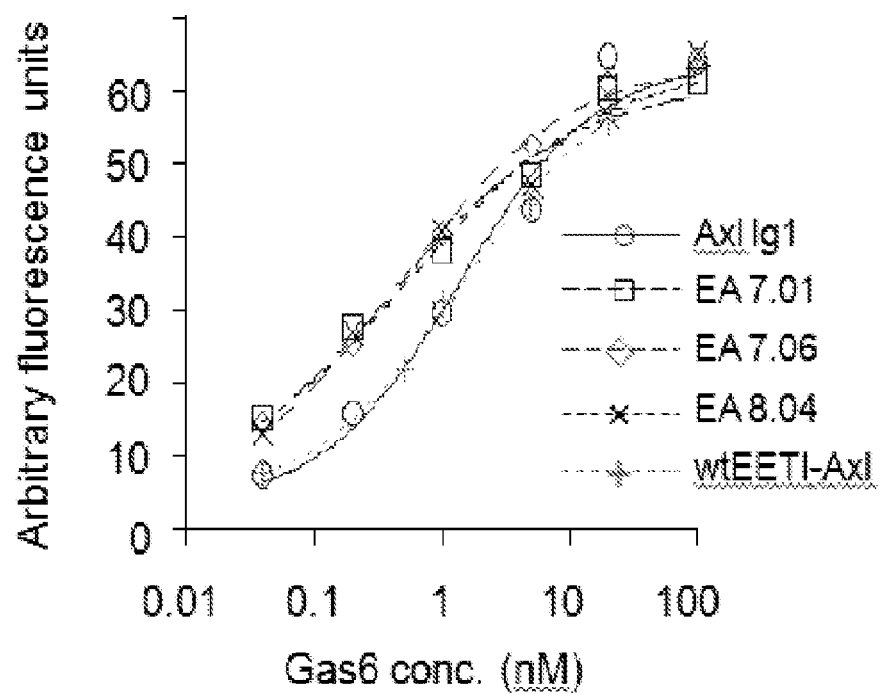
FIG. 4 is a graph that shows equilibrium binding of wild-type Axl Ig1, wild-type EET1-Axl, and EA ("EETI-II-Axl") mutants to Gas6. Representative data of experiments performed in triplicate on separate days.

The affinities of the EETI-II mutants alone were too weak to be detected, but when fused to Axl Ig1, the EA mutants exhibited subnanomolar affinities up to ~4-fold stronger than wild-type Axl Ig1. Wild-type EETI-II fused to the Axl N-terminus exhibited the same affinity as wild-type Axl. This further demonstrates the fusion construct does not interfere with the native Axl-Gas6 interaction, and that affinity improvement is due to the EETI-II loop mutants, rather than simply resulting from fusion of the EETI-II knottin to the Axl N-terminus (FIG. 4 and Table 4).

TABLE 5

Affinity of wt EETI-Axl and EA (EETI-II-axl fusion) mutants.

|  | $K_D$ (nM) | x-fold over wt |
|---|---|---|
| Wt EETI-Axl | 1.6 ± 0.3 | 1 |
| EA 7.01 | 0.46 ± 0.06 | 3.6 |
| EA 7.06 | 0.42 ± 0.11 | 3.9 |
| EA 8.04 | 0.59 ± 0.08 | 2.8 |

Affinities are reported as avg. ± std. dev. of three independent experiments.

Figure 5:
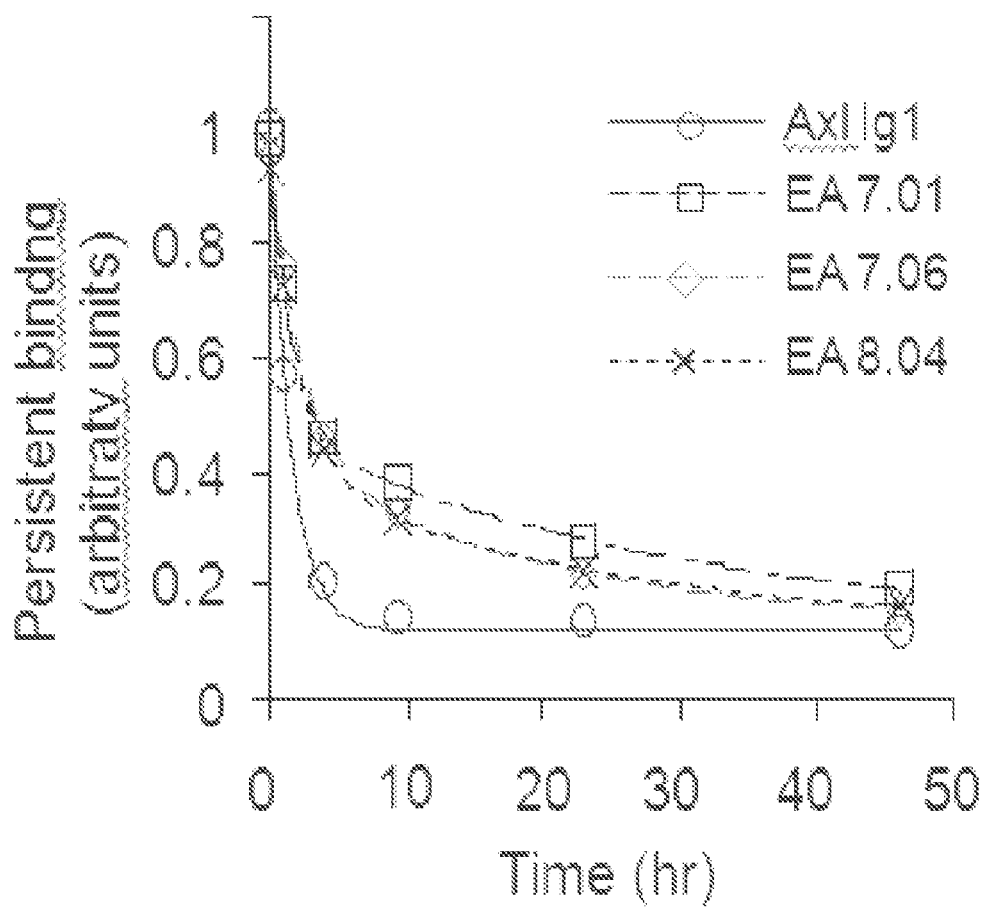
FIG. 5 is a graph that shows kinetic dissociation of wild-type Axl Ig1 or EA mutants from soluble Gas6. Wild-type Axl Ig1 was well fit by a single exponential decay model, while EA mutants had to be fit with a double-exponential decay model. Representative data of experiments performed in triplicate on separate days.

To explore the nature of the enhanced binding, we conducted binding studies to monitor dissociation kinetics. Incubation of yeast expressing either wild-type Axl Ig1 or EA mutants with 2 nM Gas6 was followed by incubation with a molar excess of competitor in a similar manner to the 'off-rate' sorts described above. While wild-type Axl Ig1 exhibits kinetic dissociation that is well-described by a single exponential decay model, the EA mutants exhibit more complex kinetics and must be fit using a double exponential decay model (FIG. 5 and Table 5). As a control, wild-type EETI-Axl exhibited indistinguishable dissociation kinetics from wild-type Axl Ig1 and was well-fit by a single exponential decay model (data not shown).

TABLE 6

Kinetic dissociation constants of wild-type Axl Ig1 and EA mutants.

|  | $k_{off,1}$ (hr) | $k_{off,2}$ (hr) |
|---|---|---|
| Wt Axl | 0.76 ± 0.16 | — |
| EA 7.01 | 0.77 ± 0.16 | 0.038 ± 0.004 |
| EA 7.06 | 0.74 ± 0.27 | 0.067 ± 0.010 |
| EA 8.04 | 0.62 ± 0.14 | 0.048 ± 0.001 |

Kinetic constants are reported as avg.±std. dev. of three independent experiments.

Figure 6A:
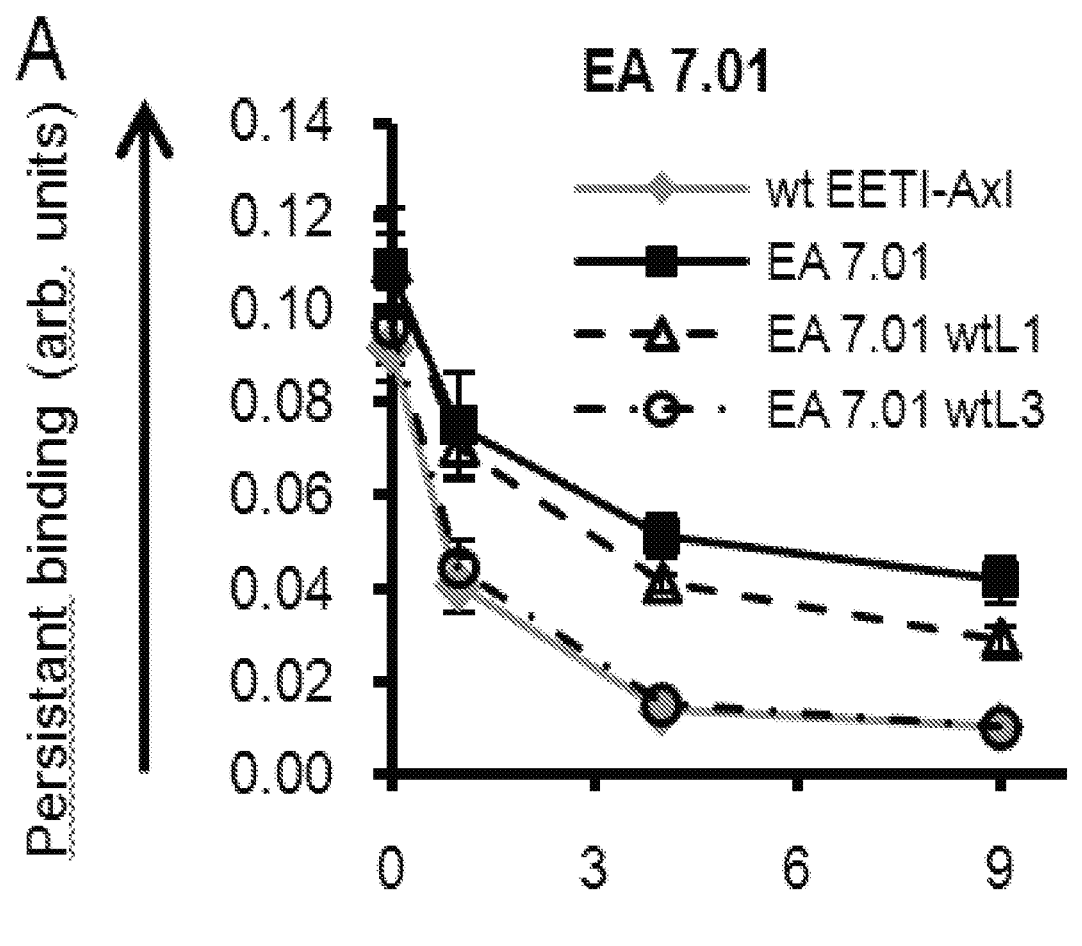
FIGS. 6A, 6B and 6C is a series of graphs that shows the contribution of individual loops in EA mutants. Reversion to wild-type for (6A) EA 7.01, (6B) EA 7.06, (6C) EA 8.04. wtL1 or wtL3 refers to wild-type EETI-II loop sequence for loop 1 or loop 3, respectively. Persistent binding for wtEETI-Axl is shown on each plot for reference and represents "reversion" of both loops 1 and loop 3 to wild-type EETI-II sequence. Data is average of experiments performed on three separate days, error bars are ±std. dev.
Figures 6B, 6C:
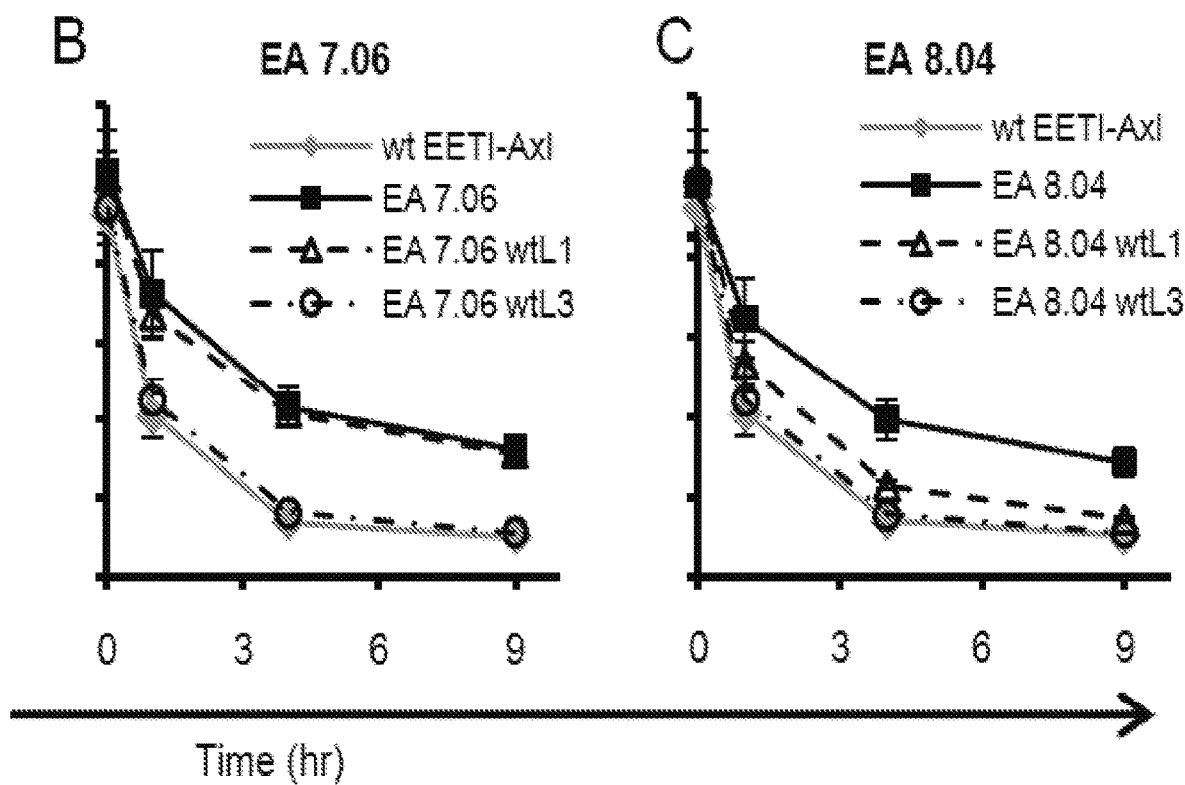

To interrogate the contributions from each of the engineered loops to the enhanced affinity, we individually reverted loops 1 or 3 of the EA mutants to the wild-type EETI-II sequence and tested binding to Gas6 (FIG. 6). In these studies wild-type EETI-Axl was used as a control for "reversion" of both loops to wild-type. Evaluation of persistent binding of EA 7.06 revealed only loop 3 contributes to the interaction with Gas6, as reversion of loop 1 to wild-type EETI-II sequence (EA 7.06 wtL1) exhibits identical persistent binding to the parental EA 7.06 mutant (FIG. 6B). For EA 7.01 and EA 8.04, reversion of loop 1 to wild-type EETI-II sequence (EA 7.01 wtL1 and EA 8.04 wtL1) exhibits weaker persistent binding than the respective parental mutants, but stronger than wild-type EETI-Axl. Reversion of loop 3 to wild-type in EA 7.01 wtL3 and EA 8.04 wtL3 completely abolished improvement over wild-type EETI-Axl (FIG. 6A&C). Together, this demonstrates that for EA 7.01 and EA 8.04, loop 3 is the main contributor, but both engineered loops are necessary for maximum enhancement of binding, and for EA 7.06 loop 3 is the sole contributor.

Example 6: Knottin Fusions with Mutated Receptor Fragment (EETI-II-Axl Ig1)

The following example describes the preparation of Axl Ig1 receptor fragments fused to mutated EETI-II knottins engineered to bind integrins, namely knottins 2.5D and 2.5F, 2.5D and 2.5F are both variants of the *Ecballium elaterium* trypsin inhibitor-II (EETI-II) knottin. These knottins were engineered to specifically hind to the $\alpha_v\beta_3$, $\alpha_v\beta_5$ and $\alpha_v\beta_3$, $\alpha_v\beta_5$, $\alpha_5\beta_1$ integrins, respectively. To accomplish this, loop 1 of EETI-II was replaced with a randomized sequence containing the integrin recognition tripeptide motif, RGD. Yeast surface display and fluorescence activated cell sorting (FACS) was then used to select for clones with the desired binding properties. These integrins are clinically important cancer targets and Axl is a receptor tyrosine kinase that is an emerging target for cancer treatment as well. Axl overexpression has been linked to invasive and metastatic phenotypes of a variety of cancers, suggesting that antagonizing the interaction between Axl and its native ligand, Gas6, could be of therapeutic value.

Axl S6-1 and S6-2 are engineered versions of Axl Ig1 that bind to Axl's native ligand, Gas6, with higher affinity than wild-type. Using error-prone PCR, mutants were introduced into the wild-type Axl Ig1 gene and the resulting mutant DNA library was expressed on the surface of yeast. Using FACS, clones with improved binding to Gas6 were isolated. Clones S6-1 and S6-2 display 20- and 12-fold improvements in equilibrium binding over wild-type, respectively, with improvements largely coming from enhanced off-rates. In addition to binding Gas6 tighter, S6-1 has a 13° C. improvement in melting temperature over wild-type representing a significant enhancement in stability.

Table 7 below shows the various peptides (EETI-II) and the Axl mutants used.

| Protein/ Scaffold | Target | Engineered Portion | SEQ ID NO: |
|---|---|---|---|
| EETI-II mutant 2.5D | αvβ3, αvβ5 | Loop 1: CPQGRGDWAPTSC | 59 |
| EETI-II mutant 2.5F | αvβ3, αvβ5, α5β1 | Loop 1: CPRPRGDNPPLTC | 60 |
| Axl Ig1* | Gas6 | None | |
| Axl S6-1* | Gas6 | G32S, D87G, V92A, G127R** | |
| Axl S6-2* | Gas6 | E26G, V79M, V92A, G127E** | |

*Axl Ig1 consists of the first Ig domain, encompassing amino acids 19-132 of full-length Axl (Genbank Accession NO. P30530)
**Locations of these mutations are further indicated for clarity by bolding and underlining in the sequences immediately below.

Amino Acid Sequences:

The amino acid sequences of wild-type EETI-II, 2.5D and 2.5F are given above. Single amino acid mutations and a deletion were introduced into the Axl Ig1 receptor fragment as shown below, where bracketed [Ap] is omitted in EA fusions shown in Table 3:

Axl Ig1:
SEQ ID NO: 61

[AP]RGTQAEESPFVGNPGNITGARGLTGTLRCQLQVQGEPPEVHWLRDG

QILELADSTQTQVPLGEDEQDDWIVVSQLRITSLQLSDTGQYQCLVFLGH

QTFVSQPGYVGLEGLP

Axl S6-1:

SEQ ID NO: 62

[AP]RGTQAEESPFVSNPGNITGARGLTGTLRCQLQVQGEPPEVHWLRDG

QILELADSTQTQVPLGEDEQGDWIVASQLRITSLQLSDTGQYQCLVFLGH

QTFVSQPGYVRLEGLP

Axl S6-2:

SEQ ID NO: 63

[AP]RGTQAGESPFVGNPGNITGARGLTGTLRCQLQVQGEPPEVHWLRDG

QILELADSTQTQMPLGEDEQDDWIVASQLRITSLQLSDTGQYQCLVFLGH

QTFVSQPGYVELEGLP

Fusion Construction:

Using standard cloning techniques, the genes encoding for the EETI-II mutant and Axl Ig1 were assembled into a single genetic construct coding for the fusion protein. The EETI-II domain was fused to the N-terminus of Axl Ig1, resulting a fusion protein consisting of an N-terminal knottin domain followed by the Axl Ig1 domain. To improve the overall flexibility of the fusion, the final proline of EETI-II and the initial alanine and proline of Axl were removed. The DNA encoding for the fusion protein was then ligated into both yeast expression and secretion plasmids. This fusion protein has been expressed on the surface of yeast to allow for binding studies, as well as produced solubly.

Data:

Briefly, yeast displayed 2.5D-Axl was used to test whether this fusion was functional. The fusion's ability to binding to soluble $\alpha_v\beta_3$ integrin and Gas6 was measured and compared to binding levels seen in 2.5D and Axl alone. The fusion displayed $\alpha_v\beta_3$ binding affinities that matched that of 2.5D, while it maintained wild-type Axl's affinity for Gas6, validating the fusion construct. Additionally, binding of each soluble target was tested in the presence of a saturating amount of the second target to test the fusion's ability to concurrently bind both $\alpha_v\beta_3$ integrin and Gas6. These binding levels were the same as when they were measured individually, suggesting that the fusion can indeed simultaneously bind to both of its targets. Finally, to confirm that the fusion is stable, it was produced solubly in the yeast *Pichia pastoris*. Purified recombinant yields were on the order of 50-75 mg per liter. These proteins were tested for their ability to bind to cells transfected to overexpress the $\alpha_v\beta_3$ integrin. They displayed equilibrium binding consistent with that previously determined for 2.5D, further validating that fusing the two protein domains did not negatively affect binding properties.

Fusion Function:

This knottin-Axl fusion will function as a multispecific molecule capable of concurrently antagonizing both integrin binding as well as the native Gas6/Axl interactions. Gas6 is a soluble ligand whereas the integrins are cell surface receptors, allowing both targets to be bound at the same time. Binding of Gas6 will sequester the soluble ligand, preventing it from associating with, and subsequently activating endogenous Axl receptor. Binding to integrin receptors will prevent them from binding to extracellular matrix proteins.

Example 7: Knottin Fusions to Improve Yields of Engineered Knottins

As described above, knottins can be difficult to produce recombinantly. By fusing them to a well-expressing protein, they can be expressed in high yields. Cleavage of the knottin can be accomplished by the inclusion of a protease site between the protein domains.

Fusion Construction:

Using standard cloning techniques, the genes encoding for the EETI-II mutant and Axl Ig1 were assembled into a single genetic construct coding for the fusion protein. Both N and C-terminal knottin fusions were created, with the Tobacco Etch Virus (TEV) recognition site, ENLYFQG (SEQ ID NO: 80), being inserted between the protein domains. The gene was then ligated into a yeast expression plasmid and transformed into the yeast *Pichia pastoris*.

Amino Acid Sequence:

underlined—EETI mutant (2.5D)

bolded—TEV recognition site italics—Axl Ig1

N-terminal fusion:

SEQ ID NO: 64

GCPQGRGDWAPTSCKQDSDCLAGCVCGPNGFCGSENLYFQG

*RGTQAEESPFVGNPGNITGARGLTGTLRCQLQVQGEPPEVHWLRDGQILE*

*LADSTQTQVPLGEDEQDDWIVVSQLRITSLQLSDTGQYQCLVFLGHQTFV*

*SQPGYVGLEGLP*

The EETI portion is underlined. The TEV recognition site is in bold.

C-terminal fusion:

SEQ ID NO: 65

*APRGTQAEESPFVGNPGNITGARGLTGTLRCQLQVQGEPPEVHWLRDGQI*

*LELADSTQTQVPLGEDEQDDWIVVSQLRITSLQLSDTGQYQCLVFLGHQT*

-continued

FVSQPGYVGLEGLP ENLYFQG

GCPQGRGDWAPTSCKQDSDCLAGCVCGPNGFCGS

Both N and C-terminal fusions were produced with purified yields of ~50 mg per liter. The purified fusions were then subjected to proteolytic cleavage by TEV, which released the knottin domains. The knottins were then further purified by FPLC to separate them from their fusion partner. It should be noted that folded, functional EETI mutant 2.5D could not be expressed in yeast without the assistance of this fusion protein.

It can be seen that the N-terminal fusion contains a linking sequence that is in bold. In addition, a direct fusions was made without the linking sequence, i.e. wherein the carboxy terminal serine of the 2.5D EETI/integrin peptide is fused directly to the arginine of the Axl Ig1 domain. By fusing EETI2.5D to Axl Ig1, a multi-specific molecule was formed, capable of binding αvβ3/αvβ5 integrins and Gas6. Analysis of the crystal structure of Axl suggested that the N-terminus was far enough away from secondary structural elements that a direct fusion to the knottin would be appropriate results using the direct fusion are described in Example 9.

Example 8: AgRP Knottin Against $\alpha_v\beta_3$ Integrin Fused to an Engineered Fragment of HGF (NK1) that Binds the Met Receptor A dual-specific fusion protein was constructed by linking the AgRP mutant, 7A, with one of the tightest binding NK1 fragments, named Aras4, Aras4 is linked at the C-terminus of AgRP7A and there is no amino acid linker between two domains.

Figures 7A, 7B:
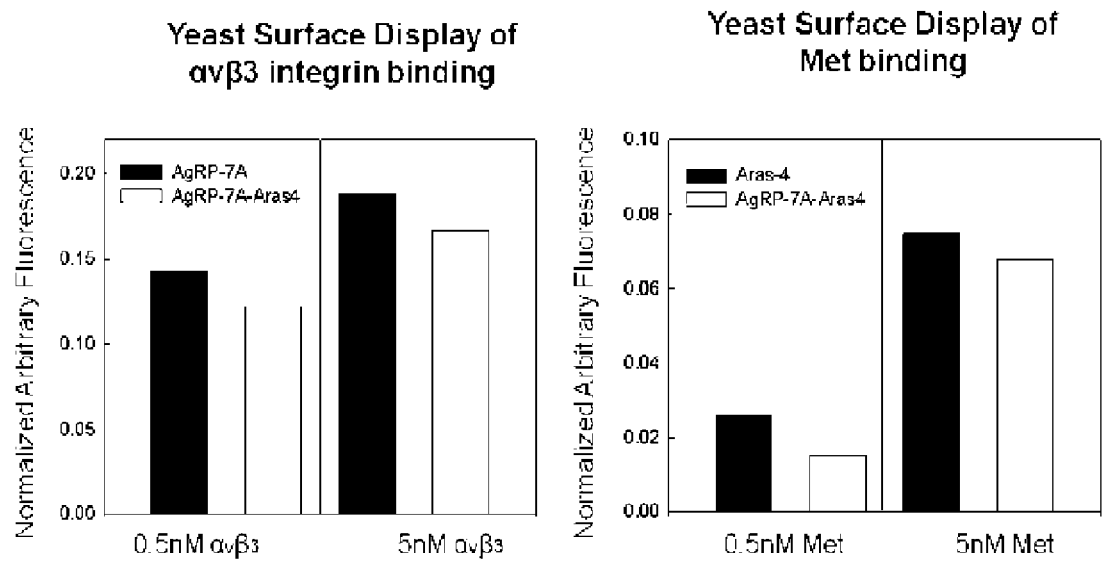
FIGS. 7A and 7B is a pair of bar graphs that shows the binding of surface displayed AgRP-Aras4 fusion protein against soluble $\alpha_v\beta_3$ integrin and Met protein compared with AgRP7A and NK1 mutant Aras4.

The binding towards soluble $\alpha_v\beta_3$ integrin and Met receptor was measured using yeast surface display. The binding against 0.5 nM and 5 nM of $\alpha_v\beta_3$ integrin and Met was measured and compared with AgRP 7A and Aras4 alone (FIG. 7). The bar graphs in FIG. 7 show that the fusion proteins have comparable binding affinities with the AgRP and NK1 mutants towards $\alpha_v\beta_3$ integrin and Met receptors, respectively. This indicates that the fusion protein can be expressed and their individual components bind to their respective targets without steric interference.

The open reading frame of the fusion protein. AgRP7A-Aras4, was incorporated into the pPICK9K plasmid and transformed into *Pichia pastoris*. The fusion protein was expressed in yeast culture according to the manufacturer's instructions (Invitrogen), then purified by metal chelating chromatography through the hexahistidine tag (SEQ ID NO: 77). The scheme of the gene of this fusion protein is show in the box below. The protein sequence of the fusion protein, AgRP7A-Aras4 is listed in Table 8 and listed below.

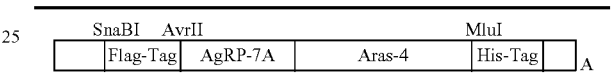

Above is a scheme of the gene of the fusion protein in pPCI9K plasmid. SnaBI, AvrII and MluI are the restriction enzyme sites.

TABLE 8

The protein sequences of Knottin-NK1 Bolded: Flag-Tag
Underlined: Knottins (AgRp7A, EETI2.5F)
Italics: NK1 variants

| Fusion Seq ID | Name of the fusion protein | Knottin | Fusion Partner | Protein sequence |
|---|---|---|---|---|
| 1 (SEQ ID NO(s): 66 | AgRP7A-Aras4 | The Agouti related protein (AgRP) | NK1 fragment of HGF (Aras4) | DYKDDDDK<u>PRGCVRLHESCLG QQVPCCDPAATCYCSGRGDND LVCYCR</u>*YAEGQGKRRNTIHEFKK SAKTTLIKIDPALRIKTEKANTADQ CANRCTRSKGLPFTCKAFVFDKA RKRCLWFPFNSMSSGVKKEFGHE FDLYENKAYIRDCIIGRGRNYRGT VSITKSGIKCQPWSAMIPHEHSFL PSSYRGEDLRENYCRNPRGEEGG PWCYTSDPEVRYEVCDIPQCSEVE TR*HHHHHH |
| 2 (SEQ ID NO: 85): | AgRP7A-M2.2 | The Agouti related protein (AgRP) | NK1 fragment of HGF (M2.2) | DYKDDDDK<u>PRGCVRLHESCLG QQVPCCDPAATCYCSGRGDND LVCYCR</u>*YAEGQRKRRNTIHEFKK SAKTTLIKIDPALKIKTEKVNTADQ CANRCTRNKG LPFTCKAFVFDKARKRCLWFPFN SMSSGVKKEFGHEFDLYENKDYI RDCIIGNGRSYRGTVSITKSGIKCQ PWSSMIP HEHSFLPSSYRGEDLRENYCRNPR GEEGGPWCFTSDPEVRYEVCDIP QCSEVETR*HHHHHH |
| 3 (SEQ ID NO: 86) | AgRp7A-M2.2 (D127A) | The Agouti related protein (AgRP) | NK1 fragment of HGF (M2.2 (D127A)) | DYKDDDDK<u>PRGCVRLHESCLG QQVPCCDPAATCYCSGRGDND LVCYCR</u>*YAEGQRKRRNTIHEFKK SAKTTLIKIDPALKIKTEKVNTADQ CANRCTRNKGLPFTCKAFVFDKA RKRCLWFPFNSMSSGVKKEFGHE FDLYENKDYIRACIIGNGRSYRGT VSITKSGIKCQPWSSMIP* |

TABLE 8-continued

The protein sequences of Knottin-NK1 Bolded: Flag-Tag
Underlined: Knottins (AgRp7A, EETI2.5F)
Italics: NK1 variants

| Fusion Seq ID | Name of the fusion protein | Knottin | Fusion Partner | Protein sequence |
|---|---|---|---|---|
| | | | | HEHSFLPSSYRGEDLRENYCRNPRGE<br>EGGPWCFTSDPEVRYEVCDIPQC<br>SEVETRHHHHHH |
| 4 (SEQ ID NO: 87): | EETI2.5F-Aras4 | Ecballium elaterium trypsin inhibitor (EETI) | NK1 fragment of HGF (Aras4) | DYKDDDDKPRGCPRPRGDNPP<br>LTCSQDSDCLAGCVCGPNGFCG<br>*YAEGQGKRRNTIHEFKKSAKTTLI<br>KIDPALRIKTEKANTADQCANRCT<br>RSKGLPFTCKAFVFDKARKRCLW<br>FPFNSMSSGVKKEFGHEFDLYEN<br>KAYIRDCIIGRGRNYRGTVSITKSG<br>IKCQPWSAMIPHEHSFLPSSYRGE<br>DLRENYCRNPRGEEGGPWCYTSD<br>PEVRYEVCDIPQCSEVETR*HHHHHH |
| 5 (SEQ ID NO: 88): | EETI2.5F-M2.2 | Ecballium elaterium trypsin inhibitor (EETI) | NK1 fragment of HGF (M2.2) | DYKDDDDKPRGCPRPRGDNPP<br>LTCSQDSDCLAGCVCGPNGFCG<br>*YAEGQRKRRNTIHEFKKSAKTTLI<br>KIDPALKIKTEKVNTADQCANRCT<br>RNKGLPFTCKAFVFDKARKRCLW<br>FPFNSMSSGVKKEFGHEFDLYEN<br>KDYIRDCIIGNGRSYRGTVSITKSG<br>IKCQPWSSMIPHEHSFLPSSYRGE<br>DLRENYCRNPRGEEGGPWCFTSD<br>PEVRYEVCDIPQCSEVETR*HHHHHH |
| 6 (SEQ ID NO: 89) | EETI2.5F-M2.2 (D127A) | Ecballium elaterium trypsin inhibitor (EETI) | NK1 fragment of HGF (M2.2 (D127A)) | DYKDDDDKPRGCPRPRGDNPP<br>LTCSQDSDCLAGCVCGPNGFCG<br>*YAEGQRKRRNTIHEFKKSAKTTLI<br>KIDPALKIKTEKVNTADQCANRCT<br>RNKGLPFTCKAFVFDKARKRCLW<br>FPFNSMSSGVKKEFGHEFDLYEN<br>KDYIRACIIGNGRSYRGTVSITKSGI<br>KCQPWSSMIPHEHSFLPSSYRGE<br>DLRENYCRNPRGEEGGPWCFTSD<br>PEVRYEVCDIPQCSEVETR*HHHHHH |

Variant sequences of the NK1 fragment could be used, and are described, e.g., in Hartman et al., "A functional domain in the heavy chain of scatter factor/hepatocyte growth factor binds the c-Met receptor and induces cell dissociation but not mitogenesis," Proc. Nat. Acad. Sci. USA Vol. 89, pp. 11574-11578. December 1992.
The detail of the protein above (SEQ ID NO: 66) is shown below:

```
Flag-Tag              AgRP7A (between slashes)
DYKDDDDKPR//GCVRLHESCLGQQVPCCDPAATCYCSGRGDNDLVCYCR//YAEG
         Loop 1 Loop 2 Loop 3    Loop 4
                      NK1

QGKRRNTIHEFKKSAKTTLIKIDPALRIKTEKANTADQCANRCTRSKGLPFTCKAFVFDKA

RKRCLWFPFNSMSSGVKKEFGHEFDLYENKAYIRDCIIGRGRNYRGTVSITKSGIKCQPWS

AMIPHEHSFLPSSYRGEDLRENYCRNPRGEEGGPWCYTSDPEVRYEVCDIPQC

SEVETRHHHHHH
```

Figure 8:
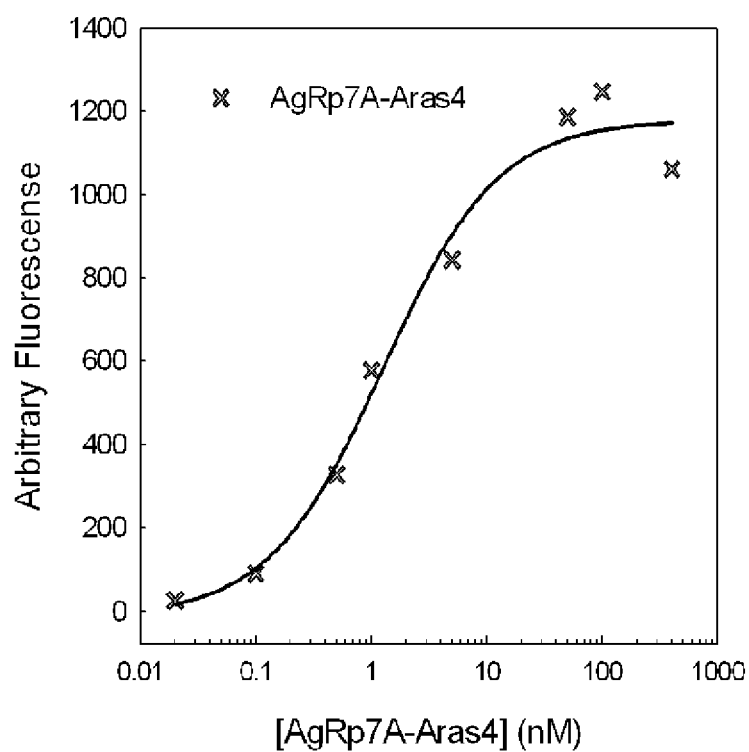
FIG. 8 is a line graph that shows binding titrations of the fusion protein, AgRP7A-Aras4 to cells that express $\alpha_v\beta_3$ integrin and Met receptor.

The His tag is underlined at the C terminus. The binding affinity of the AgRP7A-Aras4 fusion protein was measured on K562-$\alpha_v\beta_3$ cells, which express both $\alpha_v\beta_3$ integrin and Met-receptor (FIG. 8). K562 leukemia cells were previously transfected with $\alpha_v\beta_3$ integrin (Blystone, S. D. (1994). J. Cell Biol. 127, 1129-1137). We also showed by flow cytometry that these cell lines also naturally express Met receptor (data not shown).

Knottins (EETI2.5F and AgRp7A) and NK1 fusion proteins were created and purified for the study of in vitro biological characteristics. Three different NK1 variants were fused to C-terminus of the two distinct knottin proteins, including M2.2, M2.2(D127A) and Aras4. Therefore, six proteins composed of the following variations: AgRp7A-Aras4, EETI2.5F-Aras4, AgRp7A-M2.2, EETI2.5F-M2.2, AgRp7A-M2.2(D127A) and EETI2.5F-M2.2(D127A) were constructed and used for the in vitro assays. M2.2 was from the second round of directed evolution, Aras4 was from the third round of directed evolution from our previous NK1 filing. D127A is a point mutant that has previously been shown to modulate antagonistic activity).

In K562-$\alpha_v\beta_3$ cell binding assays, the binding affinities ($K_D$ values) of AgRp7A-M2.2(D127A) and EETI2.5F-M2.2 (D127A) towards the $\alpha_v\beta_3$ integrin in K562 cells transfected to express this integrin are 2.1±1.1 nM and 4.6±1.6 nM. In HUVEC cell binding assays, the binding affinities ($K_D$ values) of AgRp7A-M2.2(D127A) and EETI2.5F-M2.2 (D127A) towards human umbilical vein endothelial cells (HUVECs) are 9.4±1.0 nM and 4.7±0.6 nM. HUVECs express medium levels of the $\alpha_v\beta_3$, $\alpha_v\beta_5$ integrins, the Met receptor, and a high level of the $\alpha_5\beta_1$ integrin.

In addition, a dual receptor direct binding assay showed that multi-specific proteins bind to Met and integrins simultaneously. In this experiment, a mixture of soluble Alexa-488 labeled human Met-Fc (220 nM) and the mono-specific and the multi-specific proteins (2 or 20 nM) were added to K562-$\alpha$v$\beta$3 cells. Binding was detected by flow cytometry. AgRp7A-M2.2, EETI2.5F-M2.2, AgRp7A-M2.2(D127A) and EETI2.5F-M2.2(D127A) were able to bind to soluble Met-Fc while engaged with $\alpha_v\beta_3$ integrin on K562-$\alpha_v\beta_3$ cells. These results demonstrate that the knottin fusions can simultaneously bind to $\alpha_v\beta_3$ integrin and Met receptor.

Serum stability of AgRp7A-M2.2(D127A) and EETI2.5F-M2.2(D127A) was shown when the proteins were incubated with 40% human serum at 37° C. for over several days. Samples were analyzed by Western Blot and detected with an antibody against the FLAG epitope tag. No significant decrease in the amount of intact fusion protein was observed over 7 days, indicating stability of the knottin fusion proteins to serum proteases and elevated temperatures.

A HUVEC proliferation assay was performed where cells were stimulated with 0.5 nM HGF, AgRp7A, EETI2.5F, AgRp7A-M2.2(D127A), or EETI2.5F-M2.2(D127A) proteins were added to observe their effects on the inhibition of HUVEC proliferation. AgRp7A had little inhibitory effect on HUVECs proliferation. EETI2.5F alone showed good inhibition (70% inhibition at 1 µM, where cells alone=90% inhibition). The knottin fusion proteins AgRp7A-M2.2 (D127A) and EETI2.5F-M2.2(D127A) showed higher inhibitory effects on cell proliferation compared AgRp7A and EETI2.5F, approaching inhibition levels equivalent to that of the negative control.

A Met receptor phosphorylation assay was performed in PC3 (prostate cancer cells). Met receptor phosphorylation was assayed by Western blot after stimulation with 0.3 nM HGF. AgRp7A, Aras4 and AgRp7A-Aras4 proteins were added to observe their effects on the inhibition of Met phosphorylation. AgRp7A did not show inhibition of Met phosphorylation. Dose dependent decreases in Met receptor phosphorylation were observed upon addition of Aras4 and AgRP7A-Aras4, with slightly higher inhibitory effects observed with the AgRP7A-Aras4 knottin fusion protein. (Note: PC3 cells express medium levels of the $\alpha_v\beta_3$ integrin and Met, and low levels of the $\alpha_5\beta_1$ integrin).

Inhibition of PC3 cell adhesion to vitronectin was performed by coating human vitronectin onto the wells of a microtiter plate and seeding cells in the presence of varying concentrations of Aras4, AgRp7A. EETI2.5F, AgRp7A-Aras4, or EETI2.5F-Aras4. Half-maximal inhibitor concentration values for all constructs were similar and in the low nM range (~20-40 nM), except for Aras4, which did not inhibit PC3 cell adhesion, as expected.

Example 9: Knottin Fusion Directly Fused to Wild Type Axl Receptor Fragment

As described in Example 6, a direct fusion of the EETI knottin/integrin binding peptide to an Axl membrane bound kinase receptor was prepared. The Axl Ig1 domain, amino acids 21-132 was used. By fusing EETI2.5D to Axl Ig1, a multi-specific molecule was formed, capable of binding $\alpha$v$\beta$3/$\alpha$v$\beta$5 integrins and Gas6.

The sequence is given below, where the knottin portion, 2.5D is underlined, and the Axl portion begins with the sequence RGT . . . .

(SEQ ID NO: 84)
GCPQGRGDWAPTSCSQDSDCLAGCVCGPNGFCGS/RGTQAEESPFVGNPG

NITGARGLTGTLRCQLQVQGEPPEVHWLRDGQILELADSTQTQVPLGEDE

QDDWIVVSQLRITSLQLSDTGQYQCLVFLGHQTFVSQPGYVGLEGLP.

The ability of the fusion protein to bind to either $\alpha$v$\beta$3 integrin or Gas6 was tested using the yeast display platform, wherein the EETI2.5D-Axl fusion protein was cloned into a yeast display construct and displayed on the cell surface. Yeast expressing either EETI2.5D, Axl Ig1, or the EETI2.5D-Axl fusion protein were incubated with varying concentrations of soluble $\alpha$v$\beta$3 integrin or Gas6. The binding reactions were allowed to come to equilibrium at which time excess ligand was removed by washing. Yeast were resuspended in a solution containing fluorescently labeled antibodies against the appropriate ligand (integrin or Gas6). Flow cytometry was used to quantify bound integrin or Gas6 through the detection of the secondary antibodies. These experiments, showed that EETI2.5D and Axl Ig1 only bind $\alpha$v$\beta$3 integrin and Gas6, respectively, whereas the EETI2.5D—Axl fusion binds both proteins at levels equivalent to their mono-specific components. This data demonstrates that the fusion of EETI2.5D and Axl Ig1 does not disrupt binding to either target protein. Yeast expressing EETI2.5, wt Axl Ig1 or EETI2.5D—Axl fusion were incubated with 20, 50 or 100 nM $\alpha$v$\beta$3 integrin. As expected, only EETI2.5D and EETI2.5D—Axl bind to integrin, as wt Axl has no native affinity towards this receptor. The same set of yeast samples were incubated with 0.2, 2 or 20 nM Gas6. Wild-type Axl and EETI2.5D—Axl show affinity for Gas6, whereas no binding is detected to EETI2.5D alone. In both cases, the EETI2.5D—Axl fusion protein binds to integrin or Gas6 with affinities similar to its corresponding mono-specific components.

Next, the ability of the fusion to bind to both targets simultaneously was investigated by incubating yeast expressing EETI2.5D—Axl with $\alpha$v$\beta$3 integrin in the presence of a saturating concentration of Gas6, or with Gas6 in the presence of a saturating concentration of $\alpha$v$\beta$3 integrin. These results are outlined in FIG. 9. In both cases, the presence of an excess of the soluble second ligand does not substantially diminish binding to the primary ligand. These results indicate that binding of one target to the EETI2.5D—Axl fusion protein does not prevent binding of the second, permitting simultaneous interactions with both Gas6 and $\alpha$v$\beta$3 integrin.

Figure 9A:
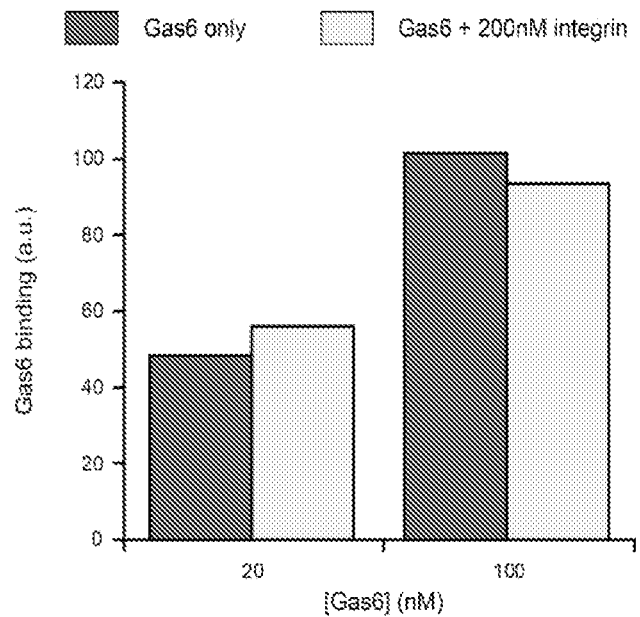
FIGS. 9A and 9B are a pair of graphs showing binding to Gas 6 (9A) and alpha v beta 3 integrin (9B) of a Axl-EETI direct fusion protein.
Figure 9B:
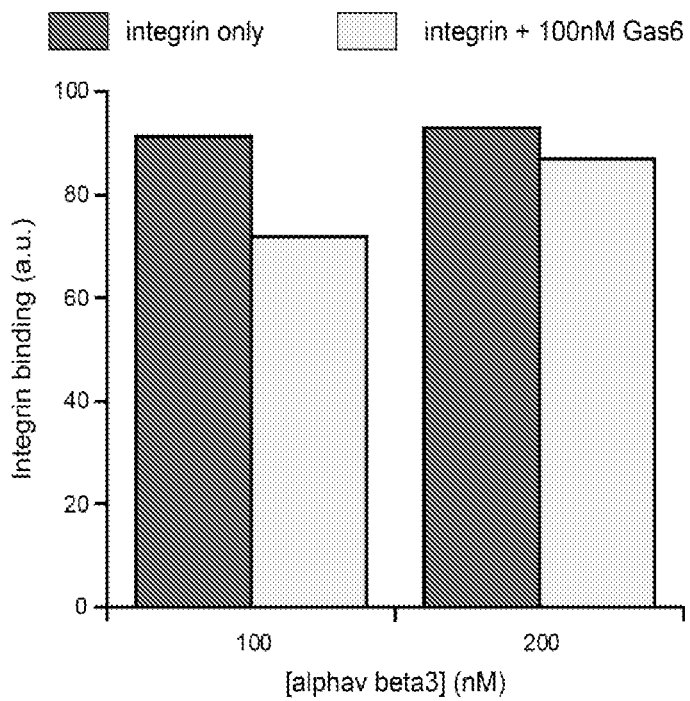

Referring to FIG. 9, yeast-surface display binding data. In FIG. 9A, yeast were incubated with 20 or 100 nM Gas6 in the presence of 200 nM $\alpha$v$\beta$3 integrin. The bispecific protein maintains affinity to Gas6 when excess integrin is present. In FIG. 9B, yeast were incubated with 100 or 200 nM αvβ3 integrin in the presence of 100 nM Gas6. Affinity to αvβ3 integrin is not lost when Gas6 is present. Together, these experiments suggest that EETI 2.5D—Axl is capable of simultaneously binding to both targets.

Example 10: Knottin Fusion Produced in Recombinant Yeast

The EETI2.5D—Axl fusion protein was then cloned into the pPic9K yeast secretion vector and soluble protein was recombinantly produced in the yeast strain P. pastoris according to the manufacturer's manual (Invitrogen). Protein was purified from culture supernatant using nickel affinity chromatography and heterogeneous yeast glycosylations were cleaved by treating the protein with endoglycosidase (endoH). Monomeric EETI2.5D—Axl protein was further purified using size exclusion chromatography. The purity of the final product was analyzed using SDS-PAGE, and analytical size exclusion chromatography. Highly pure, monomeric EETI2.5D—Axl fusion protein was obtained at an approximate yield of 35 milligrams per liter.

Recombinantly produced EETI2.5D—Axl was tested for its ability to bind cell-surface αvβ3 integrin. K562 leukemia cells that have been transfected to overexpress αvβ3 integrin (K562-αvβ3 cells) were incubated with varying concentrations of EETI2.5D—Axl. Once the reactions reached equilibrium, excess EETI2.5D—Axl was removed by washing and cells were resuspended in a solution containing a fluorescently labeled antibody against the FLAG epitope tag on the recombinant multispecific protein. Flow cytometry was then used to quantify the amount of bound EETI2.5D—Axl by detecting the fluorescent anti-FLAG antibody. The affinity (Kd) of the EETI2.5D—Axl fusion protein to the K562-αvβ3 cells was determined to be 1.72 nM. Additionally, circular dichroism spectroscopy was used to analyze the thermal stability of the EETI2.5D—Axl fusion protein as compared to wt Axl. Wild-type Axl Ig1 was found to have a melting temperature (Tm) of 41° C. By fusing EETI 2.5D to the N-terminus of Axl, an improvement of 11° C. in stability was observed (Tm~52° C.). The results of these binding studies and CD experiments are summarized in the table below.

|  | Tm (° C.) | $K_D$ to αvβ3 integrin (nM) |
| --- | --- | --- |
| wt Axl Ig1 | 41 ± 0.6 | — |
| 2.5D - Axl Ig1 | 52 ± 0.7 | 1.72 |

The specificity of the observed binding to the αvβ3 integrin expressed on K562-αvβ3 cells was tested by incubating the cells with EETI2.5D-Axl and cyclic RGD (cRGD). As EETI2.5D binds to the same epitope on the integrin as the cRGD, a molar excess of cRGD will compete off EETI2.5D—Axl if the protein is binding specifically to the integrins, cRGD inhibits the binding of EETI2.5D—Axl to K562-αvβ3 cells suggesting the protein is indeed binding specifically to αvβ3 integrin on the cell surface.

Example 11: Self-Cleaving TEV-Knottin Fusion

Several knottins are difficult to produce recombinantly as they produce high order oligomers rather than properly folded monomers. For example, while we have demonstrated robust methods for chemical synthesis and in vitro folding of EETI2.5D using solid phase peptide synthesis, we have not been able to recombinantly express this knottin in a yeast-based expression system. The observation that properly folded EETI2.5D—Axl fusions could be produced in high recombinant yield led to the development of a self-cleaving TEV-2.5D construct as a means to recombinantly produce knottins.

In this fusion, the Tobacco Etch Virus (TEV) protease was fused to the EETI knottin variant 2.5D. TEV recognizes the eight amino acid sequence, which can be either SENLYFQS or GENLYFQG (SEQ ID NO: 82) wherein glycine (G) may be substituted with serine (S) in the amino acid sequence. TEV then cuts just prior to the last G/S. This cleavage site was placed at the C-terminus of the TEV protease, followed by EETI2.5D. The first amino acid in EETI2.5D is a glycine (G), thus to eliminate extra residues from being left post-cleavage, that glycine was removed. Upon translation, the protease portion of the fusion protein can interact with the cleavage sites of another fusion, cutting it and thereby generating free EETI2.5D knottin.

This autocleaving fusion protein was cloned into the pPic9K yeast secretion vector with N and C-terminal FLAG and 6xHIS tags, respectively, and transformed into the yeast strain P. pastoris according to the manufacturer's directions (Invitrogen). Western blots on the supernatant of expression cultures were probed for either the FLAG or HIS tag. The blots revealed that probing for the N-terminal flag tag shows a high molecular weight species corresponding to the TEV protease. Blots stained for the C-terminal 6xHIS tag show a ~8 kDa species which corresponds to the cleaved knottin. Based on these expression tests, this autocleaving construct is a viable method to recombinantly express knottins which are difficult to produce in standard microbial systems.

The autocleaving construct permits recombinant production of knottins otherwise incapable of being produced in microbial systems. —This strategy could also be used to produce proteins besides knottins. Alternatively, a fusion partner such as Axl could be used to facilitate recombinant expression of knottins, with a protease cleavage site introduced in between the knottin and Axl proteins.

Example 12: Knottin-Fc Fusions

In this example, a mouse antibody Fc portion is fused to an integrin binding knottin, EETI as described above. Knottin-Fc fusions were created by molecular cloning and mammalian cell expression. These modified knottin proteins will have long circulation times (days) compared to unmodified knottins, which have half-lives on the order of minutes. Using this system, we showed that EETI-based knottin peptides 2.5D and 2.5F, and wild-type EETI-II, can be fused to an Fc domain of mouse Ig2a (SEQ ID NO: 83), and recombinantly expressed knottin-Fc fusion proteins in mammalian human embryonic kidney (HEK) cells. The Fc domain is a known sequence, see, e.g. Accession NM_010184.2 for an mRNA sequence. The knottin peptides were purified and run on a NuPAGE 4-12% Bis-Tris gel. The results showed the expected sizes of non-reduced (NR) and reduced (R) knottin 2.5D-Fc. The knottin proteins were then analyzed by gel filtration chromatography in which the purified knottin-Fc protein 2.5D showed no tendency to aggregate.

The binding of the knottin-Fc proteins to tumor cell lines were then measured. The knottin 2.5F-Fc peptide was found to bind with a greater affinity to sk0v3 cells compared to the knottin 2.5D-Fc peptide when measured against wild-type EETII-Fc. In contrast, knottin 2.5-Fc and 2.5D-Fc bound with similar affinity to K562 leukemia cells transfected with αvβ3 integrin.

Figure 10:
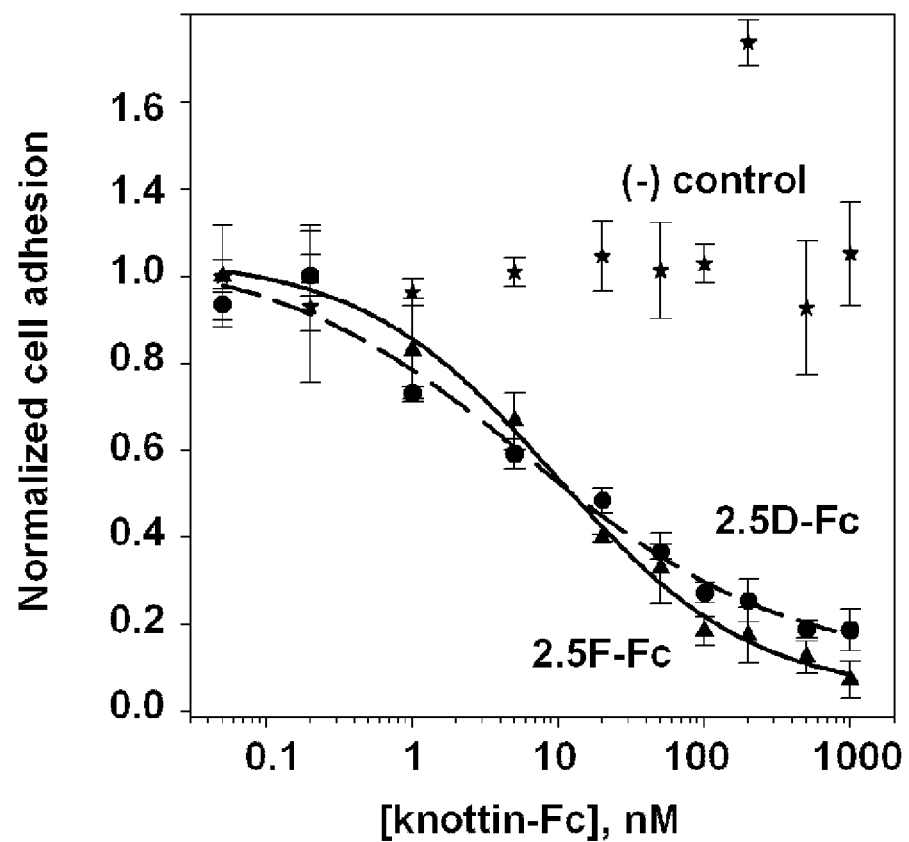
FIG. 10 is a graph that shows the inhibition of PC3 tumor cell adhesion to microtiter plates coated with vitronectin. Knottin 2.5F-Fc and 2.5D-Fc (knottin-integrin fused to Fc portions) inhibit PC3 cell adhesion with concentrations in the low nanomolar range. Negative control is an irrelevant protein.

In another tumor model, the ability of the knottin-Fc proteins to inhibit PC3 cell adhesion to the extracellular matrix (ECM) protein vitronectin was analyzed. Both of the knottin-Fc proteins strongly inhibited tumor cell adhesion, while the negative control did not. Results are shown in FIG. 10. As the inhibition of integrin-ECM adhesion induces caspase-mediated apoposis, this biological mechanism will be explored in future studies.

This work is the first demonstration that an antibody Fc domain can be fused to a knottin protein without disrupting receptor binding affinity. This strategy will be a general platform for increasing half-life of engineered knottin proteins against a variety of biomedical targets besides integrins. It is also a potential platform to make dimeric proteins (as Fc fusions am bivalent), which can have increased binding affinity and increased or altered biological potency over monovalent knottins. Furthermore. Fc fusions can be used as a framework to construct higher order oligomers or multivalent/multispecific proteins, similar to what has been done with antibody-based agents.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A recombinant soluble fusion protein, comprising:
   (a) an EETI-II knottin polypeptide having therein a binding loop having a non-native sequence for binding to a first target, wherein the non-native sequence mediates binding to one or more of (a) alpha v beta 3 integrin, (b) alpha v beta 5 integrin, and (c) alpha 5 beta 1 integrin; fused to
   (b) an extracellular domain of a receptor tyrosine kinase.

2. A method for preparing a recombinant soluble fusion protein according to claim 1, comprising the steps of:
   (a) preparing a library having a number of DNA constructs encoding the fusion protein having a number of randomized loop domains;
   (b) expressing the DNA constructs in the library in yeast to display the randomized loop domains on the yeast surface;
   (c) screening the DNA constructs for binding of the loop domains to the first target by contacting the loop domains with the first target;
   (d) selecting DNA constructs that express loop domains that bind with high affinity to the target; and
   (e) obtaining the coding sequences of the selected DNA constructs, whereby said fusion protein may be prepared.

3. The method of claim 2 wherein the second polypeptide is a tyrosine kinase receptor fragment.

4. The method of claim 2 wherein the knottin is further engineered in loop 3.

5. A method for inhibiting binding of a ligand to a receptor, comprising administering an amount of a soluble fusion protein comprising (i) a polypeptide encoding an extracellular domain of a receptor to be inhibited and (ii) a knottin polypeptide having a loop domain engineered to bind to a cell surface receptor that is not the receptor to be inhibited.

6. The method of claim 5 wherein the cell surface receptor is an integrin.

7. The method of claim 5 wherein the receptor to be inhibited is a receptor tyrosine kinase.

8. The recombinant soluble fusion protein of claim 1, wherein the knottin polypeptide comprises at least 85% amino acid sequence identity to the knottin polypeptide set forth in SEQ ID NO:33.

9. The recombinant soluble fusion protein of claim 1, wherein the knottin polypeptide comprises the amino acid sequence set forth in SEQ ID NO:33.

10. The recombinant soluble fusion protein of claim 1, wherein the knottin polypeptide comprises at least 85% amino acid sequence identity to the knottin polypeptide set forth in SEQ ID NO:32.

11. The recombinant soluble fusion protein of claim 1, wherein the knottin polypeptide comprises the amino acid sequence set forth in SEQ ID NO:32.

12. A pharmaceutical composition, comprising:
    (i) the recombinant soluble fusion protein of claim 1; and
    (ii) a pharmaceutically-acceptable carrier.

13. A pharmaceutical composition, comprising:
    (i) the recombinant soluble fusion protein of claim 8; and
    (ii) a pharmaceutically-acceptable carrier.

14. A pharmaceutical composition, comprising:
    (i) the recombinant soluble fusion protein of claim 9; and
    (ii) a pharmaceutically-acceptable carrier.

15. A pharmaceutical composition, comprising:
    (i) the recombinant soluble fusion protein of claim 10; and
    (ii) a pharmaceutically-acceptable carrier.

16. A pharmaceutical composition, comprising:
    (i) the recombinant soluble fusion protein of claim 11; and
    (ii) a pharmaceutically-acceptable carrier.

17. The recombinant soluble fusion protein of claim 1, wherein the knottin polypeptide comprises at least 90% amino acid sequence identity to the knottin polypeptide set forth in SEQ ID NO:33.

18. The recombinant soluble fusion protein of claim 1, wherein the knottin polypeptide comprises at least 95% amino acid sequence identity to the knottin polypeptide set forth in SEQ ID NO:33.

19. The recombinant soluble fusion protein of claim 1, wherein the knottin polypeptide comprises at least 90% amino acid sequence identity to the knottin polypeptide set forth in SEQ ID NO:32.

20. The recombinant soluble fusion protein of claim 1, wherein the knottin polypeptide comprises at least 95% amino acid sequence identity to the knottin polypeptide set forth in SEQ ID NO:32.

21. The recombinant soluble fusion protein of claim 1, wherein the knottin polypeptide comprises at least 70% amino acid sequence identity to the knottin polypeptide set forth in SEQ ID NO:33 or SEQ ID NO:32.

22. The recombinant soluble fusion protein of claim 1, wherein the non-native sequence comprises the amino acid sequence RGD.

23. A pharmaceutical composition comprising:
    (i) the recombinant soluble fusion protein of claim 21; and
    (ii) a pharmaceutically-acceptable carrier.

24. A pharmaceutical composition comprising:
    (i) the recombinant soluble fusion protein of claim 22; and
    (ii) a pharmaceutically-acceptable carrier.

* * * * *

UNITED STATES PATENT AND TRADEMARK OFFICE
CERTIFICATE OF CORRECTION

PATENT NO. : 10,844,106 B2
APPLICATION NO. : 13/883216
DATED : November 24, 2020
INVENTOR(S) : Jennifer R. Cochran et al.

It is certified that error appears in the above-identified patent and that said Letters Patent is hereby corrected as shown below:

In the Specification

In Column 3, Line 36, "accepts" should read --aspects--

In Column 6, Line 53, "Knotting" should read --Knottin--

In Column 7, Line 60, "EETI-TI" should read --EETI-II--

In Column 11, Line 7, "EETI-TI" should read --EETI-II--

In Column 12, Line 59, "TOG4B_AGFAP" should read --TOG4B_AGEAP--

In Column 29, Line 38, "climinating" should read --eliminating--

In Column 36, Line 12, "dctermined" should read --determined--

In Column 45, Line 18, "am" should read --are--

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*